(12) United States Patent
Riske et al.

(10) Patent No.: US 9,175,283 B2
(45) Date of Patent: Nov. 3, 2015

(54) USE POLYSACCHARIDES FOR PROMOTION OF ENZYMATIC ACTIVITY

(75) Inventors: Frank Riske, Stoughton, MA (US); Michael Hayes, Boxborough, MA (US); Gary Lazarus, Jamesville, NY (US)

(73) Assignee: Genzyme Corporation, Cambridge, MA (US)

( * ) Notice: Subject to any disclaimer, the term of this patent is extended or adjusted under 35 U.S.C. 154(b) by 1222 days.

(21) Appl. No.: 12/227,618

(22) PCT Filed: May 31, 2006

(86) PCT No.: PCT/US2006/021092
§ 371 (c)(1),
(2), (4) Date: May 29, 2009

(87) PCT Pub. No.: WO2007/139553
PCT Pub. Date: Dec. 6, 2007

(65) Prior Publication Data
US 2009/0263371 A1    Oct. 22, 2009

(51) Int. Cl.
| C12N 9/96 | (2006.01) |
| C12N 9/14 | (2006.01) |
| C08B 31/12 | (2006.01) |
| C12N 9/24 | (2006.01) |
| C12N 9/38 | (2006.01) |
| A61K 38/00 | (2006.01) |

(52) U.S. Cl.
CPC . *C12N 9/96* (2013.01); *C08B 31/12* (2013.01); *C12N 9/2402* (2013.01); *C12N 9/2471* (2013.01); *C12Y 302/01018* (2013.01); *C12Y 302/01023* (2013.01); *C12Y 302/01052* (2013.01); *A61K 38/00* (2013.01)

(58) Field of Classification Search
CPC ...... C12N 9/96; C12N 9/2471; C12N 9/2402; C12Y 302/01023; C12Y 302/01052; C12Y 302/01018; A61K 38/00; C08B 31/12
See application file for complete search history.

(56) References Cited

U.S. PATENT DOCUMENTS

| 3,937,821 | A | 2/1976 | Irikura et al. |
| 4,154,656 | A | 5/1979 | Maurer |
| 4,473,552 | A | 9/1984 | Jost |
| 4,714,611 | A | 12/1987 | Yasaburgo et al. |
| 4,837,022 | A | 6/1989 | Kakimoto et al. |
| 5,616,689 | A | 4/1997 | Shenoy et al. |
| 6,007,978 | A | 12/1999 | Goodrich, Jr. et al. |
| 6,136,578 | A | 10/2000 | Srensen et al. |
| 6,187,529 | B1 | 2/2001 | Fahy et al. |
| 6,395,270 | B1 | 5/2002 | Carlson et al. |
| 6,451,600 | B1 | 9/2002 | Rasmussen et al. |
| 6,458,387 | B1* | 10/2002 | Scott et al. ................. 424/489 |
| 6,586,573 | B1 | 7/2003 | Besman et al. |
| 6,627,275 | B1 | 9/2003 | Chen |
| 6,630,137 | B1 | 10/2003 | Carlson et al. |
| 6,835,372 | B2 | 12/2004 | Kuo et al. |
| 2003/0138437 | A1 | 7/2003 | Hunt |
| 2004/0029776 | A1 | 2/2004 | Warne et al. |
| 2005/0063943 | A1 | 3/2005 | Sommermeyer et al. |
| 2005/0169886 | A1* | 8/2005 | Brody et al. ................. 424/85.6 |
| 2005/0181985 | A1 | 8/2005 | Hemberger et al. |
| 2006/0188472 | A1 | 8/2006 | Sommermeyer et al. |
| 2006/0228348 | A1* | 10/2006 | Stefano ....................... 424/94.61 |

FOREIGN PATENT DOCUMENTS

| AR | 053507 A1 | 5/2006 |
| EP | 0150067 A2 | 7/1985 |
| EP | 1398038 A1 | 3/2004 |
| EP | 2029740 | 3/2009 |
| GB | 1519285 A | 7/1978 |
| GB | 126588 A | 3/1984 |
| JP | 52125689 A | 10/1977 |
| JP | 54-70419 A | 6/1979 |
| JP | 60-155136 A | 8/1985 |
| JP | 2009-538619 | 11/2009 |
| WO | WO 84/00891 | 3/1984 |
| WO | WO 98/40471 | 9/1998 |
| WO | WO 01/49830 A2 | 7/2001 |
| WO | WO 01/49830 A3 | 7/2001 |
| WO | WO 02/080979 A2 | 10/2002 |
| WO | WO 02/080979 A3 | 10/2002 |
| WO | WO 03/074087 A1 | 9/2003 |

OTHER PUBLICATIONS

Oct. 22, 2010, Communication pursuant to Article 94(3) EPC, 06 760 588.1.
Apr. 28, 2011, Response to Communication pursuant to Article 94(3) EPC, 06 760 588.1.
Jul. 7, 2011, Communication pursuant to Article 94(3) EPC, 06 760 588.1.
Sep. 12, 2011, Office Action, 2009-513112.
Artursson, P., et al., "Characterization of Polyacryl Starch Microparticles as Carriers for Proteins and Drugs," *J. of Pharma. Sci.*, 73(11):1507-1513 (1984).
Back, J.F., et al., "Increased Thermal Stability of Proteins in the Presence of Sugars and Polyols," *Thermal Stability of Proteins*, 18(23):5191-5196 (1979).
Cherry, J.R. and Fidantsef, A.L., "Directed Evolution of Industrial Enzymes: An Update," *Current Opinion in Biotechnology*, 14:438-443 (2003).

(Continued)

*Primary Examiner* — Taeyoon Kim
(74) *Attorney, Agent, or Firm* — Hamilton, Brook, Smith & Reynolds, P.C.

(57) ABSTRACT

This disclosure provides methods and compositions for the promotion of enzymatic activity of Target Enzymes, including but not limited to oligosaccharide/polysaccharide enzymes, protein enzymes, polynucleotide enzymes. The methods involve use of a non-naturally occurring polysaccharide (including but not limited HES) for promoting the enzymatic activity of an enzyme in liquid milieu, wherein the concentration of the polysaccharide in the composition comprising the Target Enzyme is from about 0.01% to about 55% w/v.

23 Claims, 9 Drawing Sheets

(56) References Cited

OTHER PUBLICATIONS

Friedman, Y. and Higgins, E.A., "A Method for Monitoring the Glycosylation of Recombinant Glycoproteins from Conditioned Medium, Using Fluorophore-Assisted Carbohydrate Electrophoresis", *Anal. Biochem.*, 228:221-225 (1995).

Furbish, F.S., et al., "Uptake and Distribution of Placental Glucocerebrosidase in Rat Hepatic Cells and Effects of Sequential Deglycosylation," *Biochimica et Biophysica Acta*, 673:425-434 (1981).

Gao, N. and Lehrman, M.A., "Alternative Sources of Reagents and Supplies for Fluorophore-Assisted Carbohydrate Electrophoreses (FACE)", *Glycobiology*, 13(1):1G-3G (2003).

Garzon-Rodriguez, W., et al., "Optimizing Storage Stability of Lyophilized Recombinant Human Interleukin-11 with Disaccharide/Hydroxyethyl Starch Mixtures," *J. of Pharma. Sci.*, 93(3):684-696 (2004).

Hu, G-F., "Fluorophore-Assisted Carbohydrate Electrophoresis Technology and Applications", *J. Chromatogr. A*, 705:89-103 (1995).

Jackson, P., "Fluorophore-Assisted Carbohydrate Electrophoresis a New Technology for the Analysis of Glycans", *Biochem. Soc. Trans.*, 21(1):121-125 (Feb. 1993).

Köhler, H., et al., "Die Bildung Hochmolekularer Komplexe aus Serumamylase and Kolloidalen Plasmaersatzmitteln," *Anaesthesist*, 26:623-627 (1977).

Lutz, H. and Hartung, H.J., "State of Investigation on Hydroxyethylstarch," *Acta. Anaesth. Belg.*, 35(Suppl):21-26 (1984).

Starr, C.M., et al., "Fluorophore-Assisted Carbohydrate Electrophoresis in the Separation, Analysis, and Sequencing of Carbohydrates", *J. Chromatorgr. A*, 720:295-321 (1996).

Treib, J., et al., "An International View of Hydroxyethyl Starches," *Intensive Care Med.*, 25:258-268 (1999).

Vrkljan, M., et al., "Thermal Stability of Low Molecular Weight Urokinase During Heat Treatment II. Effect of Polymeric Additives," *Pharmaceutical Research*, 11(7):1004-1008 (1994).

Wallace, C.S., et al., "Pharmacologic Management of Cystic Fibrosis," *Clinical Pharmacy*, 12:657-674 (1993).

Wang, W., "Instability, Stabilization, and Formulation of Liquid Protein Pharmaceuticals," *International Journal of Pharmaceutics*, 185:129-188 (1999).

Zopf, D. and Vergis, G., "Glycosylation: A Critical Issue in Protein Development and Manufacturing," *Pharmaceutical Vision*, pp. 10-14 (2002).

Apr. 11, 2007, Notification of Transmittal of the International Search Report and the Written Opinion of the International Searching Authority, or Declaration, PCT/US2006/021092.

Dec. 3, 2008, Notification Concerning Transmittal of International Preliminary Report on Patentability, PCT/US2006/021092.

Mar. 27, 2009, Office Action, 06 760 588.1.

Jul. 13, 2010, Reply, 06 760 588.1.

Aug. 19, 2009, Office Action, 06 760 588.1.

\* cited by examiner $R_2$ = H, $CH_2CH_2OH$
$R_3$ = H, $CH_2CH_2OH$
$R_6$ = H, $CH_2CH_2OH$, or 1,6-linkage to other α-D-glucopyranosyl units

USE POLYSACCHARIDES FOR PROMOTION OF ENZYMATIC ACTIVITY

RELATED APPLICATIONS

This application is the U.S. National Stage of International Application No. PCT/US2006/021092, filed May 31, 2006, published in English. The entire teachings of the above application(s) are incorporated herein by reference.

FIELD OF THE INVENTION

This invention relates to compositions and methods for promoting enzymatic activity by the use of a polysaccharide, including but not limited to hydroxyethyl starch. This invention further relates to methods of manufacture of proteins, which methods involve the use of enzymes. This invention further relates to methods of manufacture and/or formulation of enzymes and other biomolecules.

BACKGROUND OF THE INVENTION

Enzymes have found use in a large number of industrial applications. For example, enzymes are widely used in the detergent industry (e.g., amylases and bacterial alkaline proteases), the fruit and vegetable juice industry (e.g., pectinases and xylanases), the meat industry (e.g., xylanases, phytases, β-glucanase), the starch industry (e.g., amylases), the pulp and paper industry (e.g., xylanases), the textile industry (e.g., cellulases, polyphenol oxidases, amylases, xylanases, and catalases) and the leather industry (e.g., proteases and lipases) (Cherry et al., *Curr. Opin. Biotechnol.* 14:438-443 (2003)).

There are also a number of medical and therapeutic uses of enzymes and the nucleic acids encoding them, including for enzyme replacement therapy (ERT). In enzyme replacement therapy, a patient whose body is deficient in an enzyme activity is treated by administration of the missing (or malfunctioning) enzyme (an "ERT enzyme"). ERT enzymes are useful in the treatment of a number of diseases. For example, certain lysosomal storage disorders (LSDs) can be effectively treated by administration of an ERT enzyme.

Other examples of medically significant replacement enzymes are lactase for lactose intolerance and replacement pancreatic enzymes for the treatment of individuals with pancreatic insufficiency, including pancreatic insufficiency due to cystic fibrosis (Wallace et al., *Clin. Pharm.* 12:657-674 (1993)).

Methods of promoting enzymatic activity would be of significant value in a number of industries. With regard to the manufacture of therapeutic proteins, particularly those for human or veterinary use, it is generally desirable to use non-animal-derived components (non-ADCs). Therefore, there particularly exists a need to provide new methods and compositions for promoting the activity of enzymes with non-ADCs for diverse applications.

SUMMARY OF THE INVENTION

The present invention provides a composition comprising (a) a Target Enzyme and (b) a non-naturally occurring polysaccharide. The Target Enzyme may be e.g., an oligosaccharide/polysaccharide enzyme (i.e., an enzyme which acts on oligosaccharide(s)/polysaccharide(s)), a protein enzyme (i.e., an enzyme which acts on protein(s) such as kinases, phosphorylases), a polynucleotide enzyme (i.e., an enzyme which acts on polynucleotide(s)), or other industrially or medically relevant enzymes, including lipases and the like. The Target Enzyme may be in solution or may be immobilized on a solid support.

The non-naturally occurring polysaccharide is, in some embodiments, a modified starch. For example, the non-naturally occurring polysaccharide may be a hydroxyalkyl starch, including but not limited to hydroxyethyl starch (HES). The non-naturally occurring polysaccharide may be present at about 0.01 to 55% w/v, about 0.1% to 50% w/v, about 1% to 50% w/v, about 5% to 40% w/v, about 10% to 40% w/v, about 15% to 35% w/v, about 20% to 30% w/v, about 0.01 to about 15% w/v, about 0.1% to 15% w/v, about 1% to 10% w/v, about 5% to 15% w/v, about 3% to 7% w/v, or about 4% to 6% w/v.

Also described herein is a composition comprising (a) a Target Enzyme selected from the group consisting of oligosaccharide/polysaccharide enzymes, protein enzymes, polynucleotide enzymes, lipases, and other industrially and medically relevant enzymes, and (b) a non-naturally occurring polysaccharide, and (c) a substrate of the Target Enzyme, wherein the composition comprises from about 0.01% to 55% w/v, about 0.1% to 50% w/v, about 1% to 50% w/v, about 5% to 40% w/v, about 10% to 40% w/v, about 15% to 35% w/v, about 20% to 30% w/v, about 0.01% to about 15% w/v, about 0.1% to 15% w/v, about 1% to 10% w/v, about 5% to 15% w/v, about 3% to 7% w/v, or about 4% to 6% w/v of the polysaccharide. The substrate may be, for example, a protein, peptide, polynucleotide, nucleotide, or small molecule substrate of the Target Enzyme. In certain specific embodiments, the substrate of the Target Enzyme is itself an enzyme, including but not limited to an ERT enzyme, such as a lysosomal hydrolase.

In other specific embodiments, the invention provides a composition wherein the Target Enzyme is an oligosaccharide cleaving enzyme, the polysaccharide is HES, and the substrate is a glycoprotein. In other illustrative embodiments, the Target Enzyme is β-glucocerebrosidase, α-glucosidase, α-galactosidase, sialidase, β-galactosidase, β-N-hexosaminidase (e.g., β-N-acetylhexosaminidase) or laronidase.

The invention is also directed to methods of promoting enzymatic activity of a Target Enzyme. In one embodiment, the method comprises combining a Target Enzyme with about 0.01 to 55% w/v, about 0.1% to 50% w/v, about 1% to 50% w/v, about 5% to 40% w/v, about 10% to 40% w/v, about 15% to 35% w/v, about 20% to 30% w/v, about 0.01 to about 15% w/v, about 0.1% to 15% w/v, about 1% to 10% w/v, about 5% to 15% w/v, about 3% to 7% w/v, or about 4% to 6% of a non-naturally occurring polysaccharide, thereby producing a combination; and maintaining the combination under conditions sufficient to promote the enzymatic activity of the Target Enzyme.

The invention is also directed to use of a non-naturally occurring polysaccharide for noncryogenically promoting activity of an enzyme in liquid milieu, wherein the concentration of the polysaccharide in the composition is from about 0.01 to 55% w/v, about 0.1% to 50% w/v, about 1% to 50% w/v, about 5% to 40% w/v, about 10% to 40% w/v, about 15% to 35% w/v, about 20% to 30% w/v, about 0.01 to about 15% w/v, about 0.1% to 15% w/v, about 1% to 10% w/v, about 5% to 15% w/v, about 3% to 7% w/v, or about 4% to 6%.

The invention is further directed to enzyme formulations (including liquid formulations and reconstituted formulations) comprising a non-naturally occurring polysaccharide.

The invention is further directed to pharmaceutical compositions comprising Target Enzymes the activity of which has been promoted by a non-naturally occurring polysaccharide.

The foregoing and the following detailed description, and all examples provided, are nonlimiting.

DETAILED DESCRIPTION OF THE INVENTION

Figure 1:
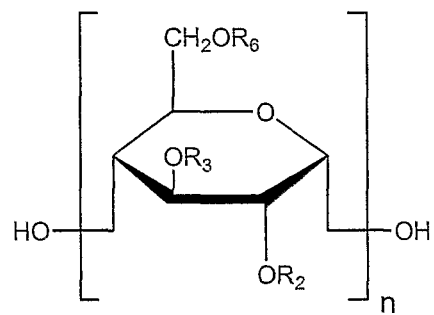
FIG. 1 depicts the polymeric structure of hydroxyethyl starch (HES). HES is a polymer of D-glucose; monosaccharide units are connected by α-1,4 linkages and by branching α-1,6 linkages that occur approximately every twenty monomer units.
Figure 2:
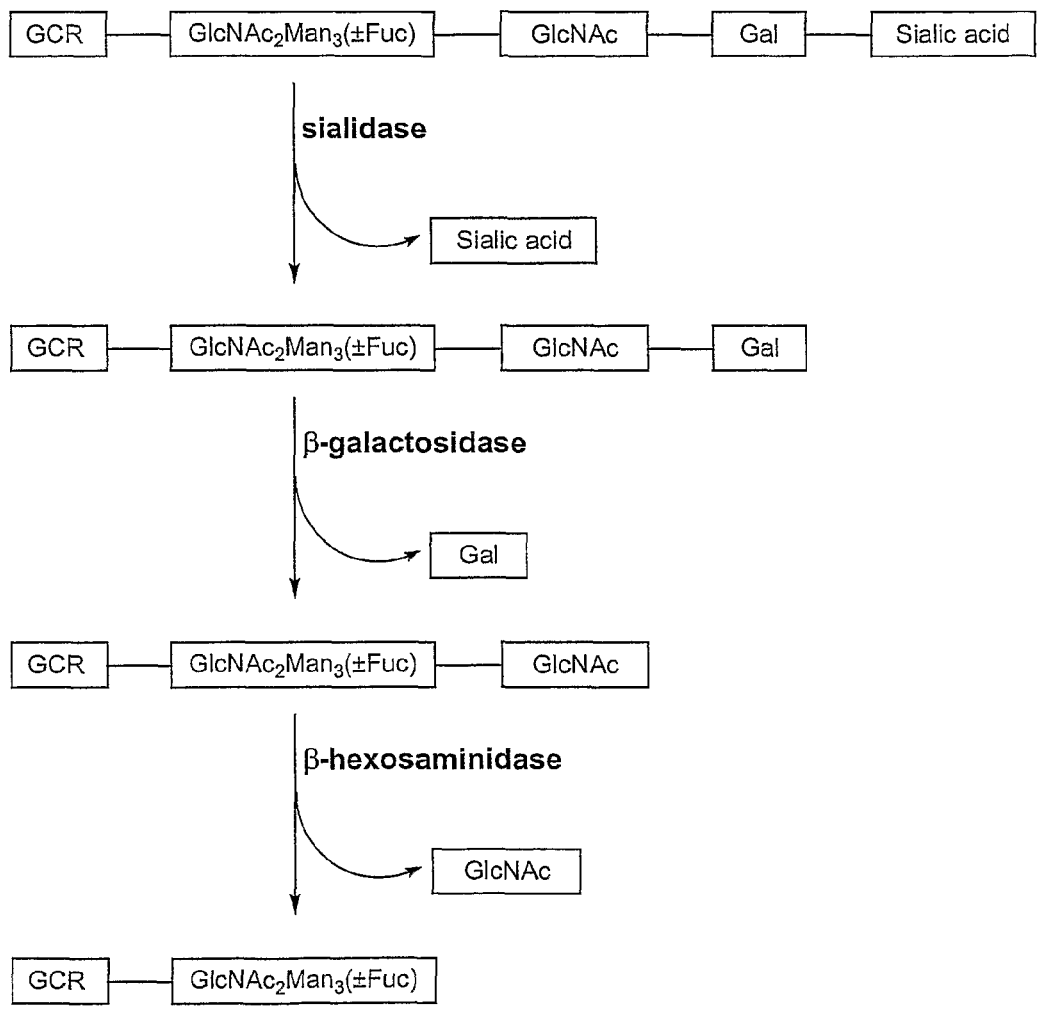
FIG. 2 depicts a process of oligosaccharide remodeling of β-glucocerebrosidase (GCR) by treatment with sialidase, β-galactosidase, and β-hexosaminidase (see, e.g., Furbish et al., *Biochim. Biophys. Acta* 673:425-434 (1981)).

There exists a need to provide new methods and compositions for promoting the activity of Target Enzymes, particularly, with non-ADCs, thus enabling the more efficient use of Target Enzymes, for diverse applications.

Nearly four hundred therapeutic proteins, including therapeutic enzymes and monoclonal antibodies, are currently under development for the treatment of human disease (Zopf et al., *Pharmaceutical Visions* 10-14 (Spring 2002)). In some cases, the manufacture of therapeutic proteins can involve enzymatic modification of the therapeutic protein itself, including but not limited to oligosaccharide remodeling, during the manufacturing process. In other cases, the therapeutic protein is itself an enzyme.

Modifications such as oligosaccharide remodeling may be desirable for optimal activity of certain therapeutic proteins. For example, Imiglucerase (the active ingredient in Cerezyme®, Genzyme Corporation, Cambridge, Mass.) is an oligosaccharide-modified human β-glucocerebrosidase (also known as GCR, acid β-glucocerebrosidase, acid β-glucosidase, glucosylceramidase, β-D-glucosyl-N-acylsphingosine glucohydrolase, EC 3.2.1.45) made using recombinant cells and is used to treat patients with Gaucher disease, a rare and devastating genetic disorder caused by a deficiency or malfunction of the β-glucocerebrosidase. Imiglucerase undergoes oligosaccharide remodeling during its manufacture: complex N-linked oligosaccharides are subjected to oligosaccharide remodeling enzymes in order to expose core mannose residues for recognition by mannose receptors on the plasma membrane of macrophages, allowing the modified GCR to be more efficiently endocytosed and delivered to macrophage lysosomes (see, e.g., Furbish et al., *Biochim. Biophys. Acta* 673:425-434 (1981)).

The present invention provides methods and compositions for promoting enzymatic activity of a Target Enzyme by combining the Target Enzyme with a polysaccharide of the invention. The present invention further provides methods and compositions for noncryogenically promoting enzymatic activity of a Target Enzyme by combining the Target Enzyme in liquid milieu (e.g., in solution or immobilized on a solid support) with a polysaccharide of the invention. Without limitation as to mechanism, the polysaccharide(s) of the invention may "promote" enzymatic activity by increasing the specific activity of the Target Enzyme by prolonging the activity of the Target Enzyme or by reducing denaturation, degradation, or aggregation of the Target Enzyme and/or stabilizing the Target Enzyme. Thus, for example, in certain embodiments of the invention use of a non-naturally occurring polysaccharide according to the methods of the invention allows use of a decreased amount of the Target Enzyme in vivo or in an enzymatic reaction in vitro, as compared to use in the absence of the polysaccharide. Enzymatic activity and enzymatic reactions can be measured by standard methods in the art (see, e.g., Eisenthal et al., *Enzyme Assays: A Practical Approach*, Oxford University Press: New York, 2002).

It has been demonstrated herein that Target Enzymes are stabilized by the presence of HES. It has also been demonstrated that HES promotes the enzymatic activity of Target Enzymes, lowers the amount of Target Enzyme needed to achieve substrate modification, and broadens the pH range at which a Target Enzyme may be used. It has also been demonstrated herein that HES is compatible with a variety of Target Enzymes and Target Enzyme concentrations; HES obtained from different commercially available sources is comparable in promoting Target Enzyme activity; and HES promotion of Target Enzyme activity is effective within a wide range of system volume.

Target Enzymes

The methods of the invention are broadly applicable to promoting the enzymatic activity of Target Enzymes. As used herein, the term "Target Enzyme" refers to an enzyme the activity of which will be or has been promoted by exposure to a non-naturally occurring polysaccharide according to the methods of this invention. However, whole blood, blood plasma, tissue plasminogen activator, interleukins, toxins, interferons, protein C, gamma globulins and collagens are specifically excluded from the definition of "Target Enzyme". One or more Target Enzymes may be used together in the methods and compositions of the invention. Whenever the term "Target Enzyme" is used, it should be appreciated that this term encompasses one or more enzymes. In certain aspects of the invention, the Target Enzyme is isolated or purified.

In some embodiments, the Target Enzyme may be an industrially relevant enzyme such as, e.g., acetolactate decarboxylase, acid proteinase, alcohol dehydrogenase, alkaline protease, amino acid oxidase, aminoacylase, aminopeptidase, α-amylase, β-amylase, aspartic β-decarboxylase, bromelain, catalase, cellulase, chloroperoxidase, cyclodextrin glycosyltransferase, β-glucanase, β-glucosidase, dextranase, dextrinase, endo-peptidase, α-galactosidase, glucoamylase, glutaminase, hemicellulase, histidase, invertase, isomerase, lactase, lyase, lysozyme, naringinase, oxireductase, pectinase, penicillin acylase, pepsin, peroxidase, pullulanase, subtilisin or the like.

In other embodiments, the Target Enzyme may be an oligosaccharide/polysaccharide enzyme that can affect a covalent bond of an oligosaccharide or a polysaccharide (see, e.g., Table 1). For example, an oligosaccharide/polysaccharide enzyme may be a glycosyltransferase or a glycosidase. In other embodiments, the Target Enzyme is a protein enzyme that can affect a protein or peptide, or its amino acid side chains, resulting in a molecular change in the protein (see, e.g., Table 2). For example, a protein enzyme may be a protease or phosphorylase. In other embodiments, the Target Enzyme is a polynucleotide enzyme that can affect a polynucleotide, or a nucleotide, resulting in a molecular change in the polynucleotide (see, e.g., Table 3). For example, a polynucleotide enzyme may be a ligase or endonuclease. For other embodiments, the Target Enzyme can effect a covalent modification to a small molecule, such as cleavage, addition, or other change to that molecule e.g., glucose isomerase which converts glucose to fructose. Thus, in certain embodiments, the Target Enzyme of the invention may be a glycosidase, glycosyltransferase, kinase, phosphatase, phosphorylase, sulfatase, acetylase, protease, nuclease, or ligase. A Target Enzyme may act in vivo or in vitro, and/or may act upon an isolated or purified oligosaccharide, polysaccharide, protein, peptide, lipid, small molecule or polynucleotide.

TABLE 1

Examples of Oligosaccharide/Polysaccharide Enzymes
Oligosaccharide/Polysaccharide Enzyme Glycosyltransferases Galactosyltransferase
GalNAc transferase
Oligosaccharyltransferase
N-acetylglucosaminylphosphotransferase
O-linked glycosyltransferase
N-linked glycosyltransferase
Exo-glycosidases α-Mannosidase
β-Galactosidase
Sialidase (neuraminidase)
β-N-acetylhexosaminidase
N-Acetyl-glucosamine-1-phosphodiester
α-N-acetylglucosaminidase
Endo-glycosidases N-Glycanase (N-glycosidase F)
O-Glycanase
(endo-α-N-acetylgalactosaminidase)
Endo-β-N-acetylglucosaminidase H
Other Sialate-O-acetyltransferase
Sialate-O-acetylesterase
α-glucosidase

TABLE 2

Examples of Protein Enzymes
Protein Enzyme

Protease
Myristoylase
Deformylase
N-Terminal methionine excision enzyme
Phosphorylase
Acetylation enzyme
Disulfide bond formation enzyme
Palmitoylation enzyme
Hydroxylation enzyme
Carboxylation enzyme
Nitration enzyme
Sulfation enzyme
ADP-ribosylation enzyme TABLE 2-continued Examples of Protein Enzymes
Protein Enzyme Deamidase
N-Linked glycosylase
O-Linked glycosylase
Glycosyl-phosphoinositolation enzyme
Farnesylase
Geranylgeranylase
Methylase
Amidation enzyme
Ubiquitination enzyme

TABLE 3

Examples of Polynucleotide Enzymes
Polynucleotide Enzyme

Exoribonuclease
Endoribonuclease
Exodeoxyribonuclease
Endodeoxyribonuclease
Restriction endonuclease
(Types I, II, and III)
Topoisomerase I
Topoisomerase II
Ligase In some embodiments, the Target Enzyme is an enzyme that modifies a therapeutic protein, i.e., a protein manufactured for the purpose of being administered to a patient as a therapeutic, prophylactic or diagnostic agent. For example, the Target Enzyme may be an oligosaccharide/polysaccharide enzyme, including but not limited to a glycosidase or glycosyltransferase. Examples of glycosidases include α-mannosidase, sialidase, β-galactosidase, β-hexosaminidase, and endo-β-galactosidase. Examples of glycosyltransferases include α-1,2-fucosyltransferase, blood group A and B transferases, and the UDP-GalNAc:polypeptide N-acetylgalactosaminyltransferases. For other examples of sugar modification enzymes, see, e.g., Table 1 and Fukuda et al., *Glycobiology: A Practical Approach*, Oxford University Press: New York, 1993; Brooks et al., *Functional and Molecular Glycobiology*, BIOS Scientific Publishers Ltd.: Oxford, UK, 2002. In certain preferred embodiments, the Target Enzyme is sialidase, β-galactosidase, and/or β-hexosaminidase.

In some embodiments, the Target Enzyme is itself a therapeutic protein. For example, Target Enzymes specifically include, but are not limited to, the ERT enzymes listed in Table 4. For example, the Target Enzyme may be β-glucocerebrosidase, α-galactosidase, or α-glucosidase. For example, as shown in Examples 1-3, glucocerebrosidase, α-glucosidase and α-galactosidase are stabilized in the presence of HES.

In some instances, the Target Enzyme can be in more than one category depending on the application for which the Target Enzyme is used.

TABLE 4

Examples of LSDs and Corresponding Defective or Deficient Enzymes

| Lysosomal storage disorder | Defective or Deficient enzyme (Lysosomal hydrolase) |
|---|---|
| Fabry | α-Galactosidase A |
| Farber | Acid ceramidase |

TABLE 4-continued

Examples of LSDs and Corresponding Defective or Deficient Enzymes

| Lysosomal storage disorder | Defective or Deficient enzyme (Lysosomal hydrolase) |
|---|---|
| Fucosidosis | Acid α-L-fucosidase |
| Gaucher types 1, 2, and 3 | Acid β-glucocerebrosidase (GCR) |
| $G_{M1}$ gangliosidosis | Acid β-galactosidase |
| Hunter | Iduronate-2-sulfatase |
| Hunter-Scheie | α-L-Iduronidase |
| Krabbe | Galactocerebrosidase |
| α-Mannosidosis | Acid α-mannosidase |
| β-Mannosidosis | Acid β-mannosidase |
| Maroteaux-Lamy | Arylsulfatase B |
| Metachromatic leukodystrophy | Arylsulfatase A |
| Morquio A | N-Acetylgalactosamine-6-sulfate sulfatase |
| Morquio B | Acid β-galactosidase |
| Niemann-Pick | Acid sphingomyelinase |
| Pompe | Acid α-glucosidase |
| Sandhoff | β-Hexosaminidase B |
| Sanfilippo A | Heparan N-sulfatase |
| Sanfilippo B | α-N-Acetylglucosaminidase |
| Sanfilippo C | Acetyl-CoA: α-glucosaminide N-acetyltransferase |
| Sanfilippo D | N-Acetylglucosamine-6-sulfate sulfatase |
| Schindler-Kanzaki | α-N-acetylgalactosaminidase |
| Sialidosis | Sialidase |
| Sly | β Glucuronidase |
| Tay-Sachs | β-Hexosaminidase A |

Lysosomal storage disorders are a class of genetic diseases, comprising over forty disorders that relate to a deficiency in lysosomal hydrolase activity. The lysosome serves as a major degradative compartment of the cell and contains multiple enzymes necessary to carry out this function. A hallmark feature of LSDs is the abnormal accumulation of metabolites in the lysosomes which leads to the formation of large numbers of distended lysosomes. Accordingly, an LSD may be treated with the administration of an ERT enzyme corresponding to the defective or deficient lysosomal hydrolase correlated with the particular LSD.

For example, as discussed above, Imiglucerase (the active ingredient in Cerezyme®, Genzyme Corporation, Cambridge, Mass.) is an oligosaccharide-modified human β-glucocerebrosidase (also known as GCR, acid β-glucocerebrosidase, acid β-glucosidase, glucosylceramidase, β-D-glucosyl-N-acylsphingosine glucohydrolase, EC 3.2.1.45) made using recombinant cells and is used to treat patients with Gaucher disease, a rare and devastating genetic disorder caused by a deficiency or malfunction of the β-glucocerebrosidase. As shown in Example 1, β-glucocerebrosidase is stabilized by the presence of a non-naturally occurring polysaccharide such as HES.

Alglucosidase Alfa, (also known as α-glucosidase, Alpha-glucosidase, or acid alpha glucosidase, CAS Reg: 420784-05-0, EC 3.2.1.3), the active ingredient in Myozyme®, (Genzyme Corporation, Cambridge, Mass.) is an ERT enzyme for the treatment of Pompe disease, a rare, debilitating, progressive disease which is often fatal. Pompe disease (glycogen storage disease type II, GSD II, glycogenosis type II, acid maltase deficiency) is an inherited disorder of glycogen metabolism caused by the absence or marked deficiency of the lysosomal enzyme, acid alpha glucosidase (GAA). As shown in Example 2, α-glucosidase is stabilized by the presence of a non-naturally occurring polysaccharide such as HES.

Another example of an ERT enzyme is Fabrazyme® (agalsidase beta) which is used to treat Fabry disease. People with Fabry disease are missing or have insufficient quantities of an essential enzyme called alpha-galactosidase A, or alpha-GAL, which helps the body to break down a fatty substance called globotriaosylceramide (GL-3). Fabrazyme® (agalsidase beta), a replacement for the missing enzyme, acts like the naturally occurring alpha-GAL enzyme and targets GL-3 inside the cell. Once inside the cell, it breaks up the GL-3 into smaller components that can then be removed from the cell by natural processes. As shown in Example 3, α-galactosidase is also stabilized by the presence of a non-naturally occurring polysaccharide such as HES.

Yet another example of an ERT enzyme is Aldurazyme® (laronidase) which is used to treat Mucopolysaccharidosis I (MPS I), a rare, autosomal recessive genetic disease that affects multiple organ systems and tissues. The disease is caused by a defect in the gene coding for the lysosomal enzyme alpha-L-iduronidase. As a result of this defect, the cells of people with MPS I are either unable to produce the enzyme or produce it in low amounts, which results in an inability of the lysosome to act in the stepwise degradation of certain glycosaminoglycans (GAG)—namely dermatan sulfate and heparan sulfate.

In some embodiments, the Target Enzyme is in liquid milieu, i.e., in a liquid or partially liquid environment. A Target Enzyme in liquid milieu may be immobilized on a solid support or may be dispersed, partially dissolved, or dissolved in solution. A Target Enzyme is immobilized on a solid support if it is bound, covalently or noncovalently, directly or indirectly, to a solid or semi-solid material, e.g., a resin. For example, the Target Enzyme may be immobilized on a solid support, e.g., by physical adsorption or a covalent bond, or through an interaction with an entity that is directly contacted with the solid support. Exemplary solid supports are well known in the art. For example, a Target Enzyme may be immobilized on a solid support by a hydrophobic interaction, an electrostatic interaction, a metal ion-ligand interaction, a small molecule interaction, a peptide-interaction, a pseudo-affinity interaction, an antigen-antibody reaction or other affinity interaction. In preferred embodiments, the solid support is insoluble in the liquid milieu, aqueous or otherwise, containing the Target Enzyme and polysaccharide (and optionally the substrate).

In some embodiments, a substrate of the Target Enzyme is present with the Target Enzyme. The substrate may be immobilized on a solid support or may be dispersed, partially dissolved, or dissolved in solution. The substrate may be, for example, a protein, peptide, polynucleotide, nucleotide, lipid, or small molecule. In some embodiments, the substrate is itself an enzyme, including but not limited to a lysosomal hydrolase such as those listed in Table 4. In embodiments wherein the substrate is an enzyme, the substrate may also be a Target Enzyme.

As is well known in the art, enzymes are typically active at particular ranges of pH, temperature, and substrate concentration. In some embodiments, for example, the pH activity range for a Target Enzyme of the invention may be from about: pH 3 to pH 9, pH 3 to pH 6, pH 4 to pH 8, pH 5 to pH 7, or pH 5.5 to pH 6.5. In some embodiments, for acidophilic enzymes, the pH may be an acidic pH (e.g., below a pH of about 6.5, 5.5, 4.5, 3.5, or 2.5). In other embodiments, for alkalophilic enzymes, the pH may be a basic pH (e.g., above a pH of about 7.5, 8.5, 9.5, 10.5, or 11.5). In some embodiments, for example, the temperature range for a Target Enzyme of the invention may be from about: 2-50° C., 10-37° C., 15-32° C., or 20-30° C. In some embodiments, for thermophilic enzymes, the temperature is above a temperature of about: 37° C., 45° C., 50° C., 60° C., 75° C., or 85° C. In other embodiments, for mesophilic enzymes, the temperature is about: 20-40° C., 25-37° C., or 30-35° C. In yet other embodiments, for psychrophilic enzymes, the temperature is below a temperature of about 30° C., 25° C., 20° C., 10° C., or 5° C. In some embodiments, for example, the enzyme to substrate ratio may be from about: 1:1,000,000,000, 1:1,000,000, 1:100,000, 1:10,000, 1:1000, 1:100, 1:10, or 1:1.

Generally, however, enzyme kinetics are understood to be governed by the principles of Michaelis-Menten kinetics, see, e.g., Lehninger Principles of Biochemistry, 3rd Edition, David L. Nelson et al Eds, Worth Publishers, NY, N.Y.

Accordingly, using such principles, one of ordinary skill in the art may determine the kinetics of a Target Enzyme through simple and routine experimentation. Additionally, enzyme information and nomenclature information is available at the Swiss-Prot. *Enzyme Nomenclature Database*—ExPASy (Expert Protein Analysis System), Release 37, March 2005, and updates up to 2 Aug. 2005au.expasy.org/enzyme/; see also, Bairoch A. *The ENZYME database in* 2000. Nucleic Acids Res. 28:304-305 (2000). See also, *Nomenclature Committee of the International Union of Biochemistry and Molecular Biology* (*NC-IUBMB*), update 27 Jul. 2005, www.chem.qmul.ac.uk/iubmb/enzyme/; see also printed version: *Enzyme Nomenclature* 1992 [Academic Press, San Diego, Calif., ISBN 0-12-227164-5, 0-12-227165-3] with Supplement 1 (1993), Supplement 2 (1994), Supplement 3 (1995), Supplement 4 (1997) and Supplement 5 (in *Eur. J. Biochem.* 1994, 223:1-5; *Eur. J. Biochem.* 1995, 232:1-6; *Eur. J. Biochem.* 1996, 237:1-5; *Eur. J. Biochem.* 1997, 250:1-6, and *Eur. J. Biochem.* 1999, 264:610-650; respectively).

Polysaccharides

A polysaccharide is a linear or branched polymer of monosaccharides, of natural or synthetic origin, comprising two or more monosaccharide units. In certain embodiments the polysaccharides of the invention comprise at least about 5, 10, 20, 30, 50, 75 or more units. In certain aspects of the invention, the monosaccharide units which make up a polysaccharide are non-identical units. Polysaccharide hydrolysis products and mixtures of polysaccharides are encompassed by the term polysaccharide as used herein.

A non-naturally occurring polysaccharide refers to a polysaccharide that has been modified from its natural state. That is, the chemical structure and/or biological activity of the non-naturally occurring polysaccharide is modified compared to the chemical structure and/or biological activity of the polysaccharide in its natural state (prior to modification). For example, hydrophilic functional groups are added to a polysaccharide molecule in order to improve solubility (e.g., to obtain a non-naturally occurring polysaccharide that is about 0.5%, 1%, 2%, 3%, 4%, 5%, 10%, 15%, 20%, 25%, 30%, 35%, 40%, 45%, 50%, 55%, 60% soluble in aqueous solution). In addition, obtain anionic or cationic functional groups can be added to a polysaccharide molecule. Suitable methods used to produce a non-naturally occurring polysaccharide (e.g., use of heat and/or chemical means) are known to those of skill in the art.

Although the majority of the discussion herein refers to non-naturally occurring polysaccharides, including but not limited to modified hydroxyalkyl starches or Ficoll®, it is appreciated that naturally occurring polysaccharides, including but not limited to α-amylose, amylopectin, or dextran can be used in the compositions and methods of the present invention.

In some embodiments, the polysaccharide is a non-naturally occurring starch, such as a chemically modified starch, including but not limited to hydroxyalkyl starches (including but not limited to HES or hydroxypropyl starch), carboxymethyl starches, diethylaminoethyl starch, (hydroxypropyl) trimethylammonium chloride starch, cyanoethyl starch, benzyl-starch, or acetyl starch (see, e.g., Hjermstad "Starch Hydroxyethyl Ethers and Other Starch Ethers" In: Whistler et al., Eds., *Industrial Gums*, Academic Press: New York, 1973 and Moser, "Hydroxyethylated Starches." In Wurzburg, Ed., *Modified Starches: Properties and Uses*, CRC Press: Boca Raton, Fla., 1987).

In certain embodiments, the polysaccharide is a hydroxyalkyl starch selected from the group consisting of hydroxymethyl starch, HES, hydroxypropyl starch, and hydroxybutyl starch.

The compositions and methods of the invention may contain or use from about 0.1% to about 55% (w/v) of the polysaccharide. In certain embodiments, the polysaccharide concentration may be from about 0.01% to 55% w/v, about 0.1% to 50% w/v, about 1% to 50% w/v, about 5% to 40% w/v, about 10% to 40% w/v, about 15% to 35% w/v, about 20% to 30% w/v, about 0.01 to about 15% w/v, about 0.1% to 15% w/v, about 1% to 10% w/v, about 5% to 15% w/v, about 3% to 7% w/v, or about 4% to 6% w/v. In certain embodiments, the polysaccharide concentration is at least about 5% (w/v). In other embodiments, the polysaccharide concentration is (w/v) at least 2%, 4%, 5%, 6%, 7%, 9%, 11%, 13%, 15%, 20%, 30% or 40% wherein the polysaccharide concentration is less than 55% (w/v). In light of the disclosure herein, the particular polysaccharide concentration which promotes activity of a particular Target Enzyme may be determined by one of ordinary skill in the art through simple and routine experimentation.

As one of skill in the art will recognize, the average molecular weight ("AMW") of the polysaccharide of the invention will depend upon the particular polysaccharide used. Generally, however, the average molecular weight of the polysaccharide(s) of the invention can vary, e.g., from about: 20 kDa to 2,600 kDa, 100 kDa to 2,000 kDa, 300 kDa to 1,500 kDa, or 400 kDa to 800 kDa. In a preferred embodiment, the average molecular weight of the polysaccharide is from about 400 kDa to about 800 kDa. In another preferred embodiment, the average molecular weight of the polysaccharide is from about 450 kDa to about 800 kDa. In another preferred embodiment, the average molecular weight of the polysaccharide is from about 400 kDa to about 750 kDa. As one of skill in the art will recognize, generally, a lower molecular weight range of a polysaccharide will have a greater solubility (w/v, w/w) versus a higher molecular weight polymer of that same polysaccharide.

In some preferred embodiments, the polysaccharide of the invention is HES. HES is a polymer that may be prepared from the plant-derived starch amylopectin, a polymer of D-glucose derived, e.g., from corn, potatoes, or wheat, by hydroxyethylation, e.g., by treatment with ethylene oxide and a metal alkoxide, and hydrolysis, e.g., with hydrochloric acid (see, e.g., Hjermstad "Starch Hydroxyethyl Ethers and Other Starch Ethers." In: Whistler et al., Eds., *Industrial Gums*, Academic Press: New York, 1973 and Lutz et al., *Acta Anaesthesiol. Belg.* 35 (Suppl.):21-26 (1984). The structural formula of HES is depicted in FIG. 1. Without limitation, the glucose units of HES are generally connected by α-1,4 linkages, and by branching α-1,6 linkages that occur approximately every 20 monomer units. HES is commercially available from several sources (see Examples herein). One benefit of HES is that it is generally considered to be safe and non-toxic, and is approved as an indirect food additive and as a blood plasma extender (see, e.g., Moser, "Hydroxyethylated Starches." In Wurzburg, Ed., *Modified Starches: Properties and Uses*, CRC Press: Boca Raton, Fla., 1987 and Treib et al.,

*Intensive Care Med.* 25:258-268 (1999)). HES is also non-animal derived. Accordingly, HES is particularly useful in the methods and compositions of the invention when applied to the manufacture of therapeutics or other agents for human use.

HES can differ in its average molecular weight and extent of hydroxyethylation. The average molecular weight can be reported as a number-average molecular weight or a weight-average molecular weight. The extent of hydroxyethylation can be measured as a molar substitution ratio ("MS"; the number of hydroxyethyl groups per glucose unit) or as a degree of substitution ("DS"; the fraction of glucose units that contain hydroxyethyl groups). Although the MS and the DS are not identical, the terms are frequently interchanged in the literature. The MS and DS of a given sample are comparable when the values are small, but the MS is greater than the DS when the sample is more highly substituted. A particular HES can be identified by its weight-average molecular weight (in kDa) and MS; for example, a HES may be reported as a HES 480/0.7, HES 450/0.7, HES 200/0.5, or HES130/0.4. For further information, see, e.g., Thompson, "Hydroxyethyl Starch." In Hennessen, Ed., *Developments in Biological Standardization Vol.* 48, S. Karger: Basel, Switzerland; Moser, "Hydroxyethylated Starches." In Wurzburg, Ed., *Modified Starches: Properties and Uses*, CRC Press: Boca Raton, Fla., 1987; and Treib et al., *Intensive Care Med.* 25:258-268 (1999). HES variants include but are not limited to (in order of increasing AMW) Tetrastarch™, pentastarch, hexastarch, and hetastarch.

In preferred embodiments, the polysaccharide is HES (e.g., HES 480/0.7 or HES 450/0.7). HES, in general, has a weight-average MW (AMW) of approximately 400-550 kDa, and an average MS of approximately 0.7. In certain embodiments, HES has a weight-average MW (AMW) of approximately 500, 550, 600, 650, 750 or 800 kDa. In certain embodiments, about 70%, 75%, 80% or more of the molecules are in the range of 20 kDa to 2,600 kDa. In certain embodiments, the MS is approximately 0.6, 0.65, 0.7, 0.75, 0.8, or 0.85.

In yet other preferred embodiments, the polysaccharide of the invention has one or more of the following characteristics:
    a) the polysaccharide is substantially soluble in the liquid milieu containing the Target Enzyme;
    b) the polysaccharide is substantially soluble in the liquid milieu containing the Target Enzyme and a substrate of such Target Enzyme;
    c) the polysaccharide is not reactive with the Target Enzyme (other than to promote enzyme activity);
    d) the polysaccharide is not reactive with the substrate of the Target Enzyme (other than to promote enzyme activity when the substrate is a Target Enzyme);
    e) the polysaccharide is stable at the temperature and/or pH in which the Target Enzyme is active or is being used;
    f) the polysaccharide is not conjugated to the Target Enzyme;
    g) the polysaccharide is not conjugated to the substrate of the Target Enzyme;
    h) the polysaccharide is non-animal derived;
    i) the polysaccharide comprises at least 2 non-identical monosaccharide units;
    j) the polysaccharide in combination with the Target Enzyme is maintained in a non-frozen state during at least a portion, preferably a substantial portion, of the promotion of enzymatic activity by the polysaccharide;
    k) the polysaccharide in combination with the Target Enzyme (and optionally substrate) is not lyophilized during at least a portion, preferably a substantial portion, of the promotion of enzymatic activity by the polysaccharide;
and/or
    l) particularly in the case of a Target Enzyme which is a therapeutic protein, the polysaccharide is non-toxic to animals and/or humans.

As used herein, "polysaccharide is not reactive with" a Target Enzyme or substrate includes but is not limited to, not inactivating the Target Enzyme or substrate, not inhibiting the Target Enzyme or substrate, not cleaving the Target Enzyme or substrate, or not degrading the Target Enzyme or substrate.

Use of the Polysaccharides

The present invention provides methods for promoting the enzymatic activity of a (one or more) Target Enzyme, in liquid milieu, with a polysaccharide(s). The methods may be performed at temperatures at which a Target Enzyme is active, including but not limited to between about: 1° C. to 40° C., 1° C. to 20° C., 15° C. to 35° C., 5° C. to 30° C., 10° C. to 30° C., or 20° C. to 30° C. In certain embodiments, the methods are performed at room temperature, i.e., at temperatures of 25° C.±about 5° C.

Figure 3:
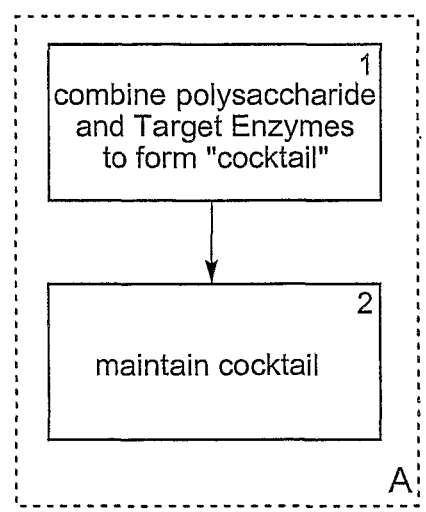
FIG. 3 is a flow-chart illustrating one embodiment of the methods of the invention, wherein Target Enzyme activity is promoted by a polysaccharide of the invention.

One embodiment of a method of the invention is depicted in FIG. 3. In this embodiment, a Target Enzyme and polysaccharide are combined to form a cocktail (step 1) and then maintained for a period of time (step 2) sufficient to promote Target Enzyme activity compared to the Target Enzyme activity in the absence, of the polysaccharide. Optionally, the cocktail may contain a substrate for the Target Enzyme. In the optional embodiment, the cocktail may be maintained during enzymatic reaction between the Target Enzyme and the substrate. In such embodiments, the Target Enzyme or substrate may be in solution, immobilized on a solid support or both.

Figure 4:
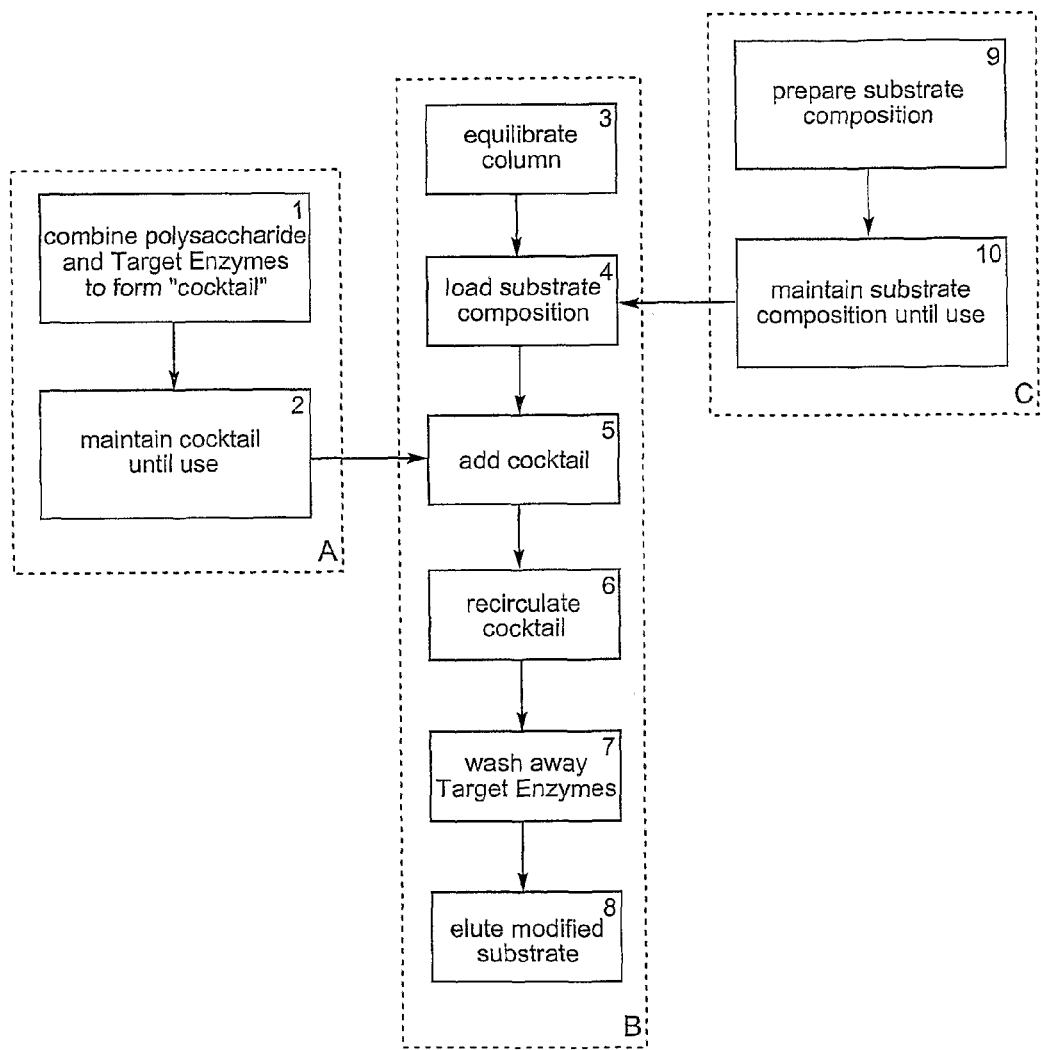
FIG. 4 is a flow-chart illustrating one embodiment of the methods of the invention, wherein the Target Enzyme is in solution and the substrate is immobilized on a solid support.

An alternate embodiment of a method of the invention is depicted in FIG. 4. In this embodiment, the activity of a Target Enzyme in a liquid milieu is promoted by a polysaccharide in the presence of a substrate, wherein the substrate is immobilized on a solid support, such as a resin packed within a column. The preparation of a Target Enzyme cocktail (process A) includes combining the polysaccharide with the Target Enzyme (step 1) to prepare a "cocktail," and maintaining the cocktail until use (step 2). A substrate composition is prepared (Process C, step 9) and maintained until use (step 10). The column is optionally first equilibrated (step 3) and the substrate is loaded onto the column (step 4). The Target Enzyme cocktail is then added to the column (step 5), and optionally recirculated through the column (step 6), allowing the Target Enzyme to modify the substrate. For example, the Target Enzyme cocktail may be recirculated through the column for a period of time including but not limited to from about 1 to 240 hours, 1 to 40 hours, 5 to 35 hours, 10 to 30 hours, 15 to 30 hours, or 19 to 25 hours. Alternatively, depending upon the kinetics of the enzymatic reaction, the Target Enzyme cocktail may be recirculated through the column for a period of time including but not limited to from about: 1-48 hours, 1-24 hours, 1-12 hours, 1-6 hours or 1-3 hours or less than about 1 hour. Once a desired level of modification is achieved, the Target Enzyme cocktail is preferably washed off the column, and the modified substrate is eluted and recovered. Other variations of this embodiment are also within the scope of the invention. For example, Process A may be eliminated from the embodiment shown in FIG. 4 and the polysaccharide may be added directly to the column either before, after or at the same time the Target Enzyme is added to the column. In other embodiments, the solid support or resin is not in the form of a column, but is e.g., in the form of a slurry, batch or other form.

Figure 5:
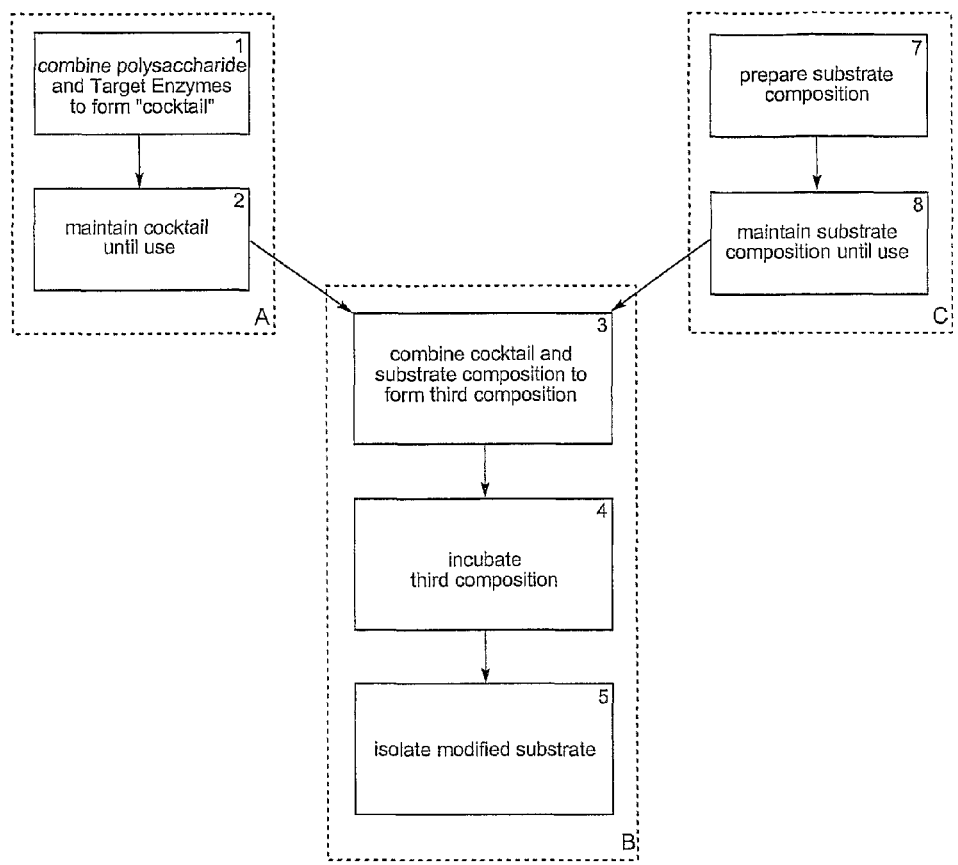
FIG. 5 is a flow-chart illustrating one embodiment of the methods of the invention, wherein the Target Enzyme and substrate are in solution.

Another embodiment of a method of the invention is depicted in FIG. 5. In this embodiment, the enzymatic activity of a Target Enzyme in solution is promoted by a polysaccharide in the presence of a substrate in solution. In certain aspects, the preparation of a Target Enzyme cocktail (process A) includes combining the polysaccharide with the Target Enzyme (step 1) and maintaining the cocktail until use (step 2). In process C, a substrate composition is prepared (step 7) and maintained until use (step 8). The Target Enzyme cocktail and the substrate composition are combined (process B, step 3) to prepare a third composition comprising the Target Enzyme, polysaccharide, and substrate. The third composition is incubated (step 4) (in some embodiments with stirring, bubbling, or gentle agitation), allowing the Target Enzyme to modify the substrate. The third composition may be incubated for a period of time including not limited to from about: 1 to 240 hours, 1 to 40 hours, 40 to 100 hours, 5 to 35 hours, 10 to 30 hours, 30 to 60 hours, 15 to 30 hours, or 19 to 25 hours. Alternatively, the Target Enzyme cocktail may be incubated for a period of time including but not limited to from about: 1-48 hours, 1-24 hours, 1-12 hours, 1-6 hours or 1-3 hours or less than about 1 hour. Once a desired level of modification is achieved, the Target Enzyme is separated from the modified substrate (step 5). Optionally, the extent of modification may be monitored during the process by, e.g., removing an aliquot of the reaction mixture and probing the modification state using an appropriate analytical method or enzymatic assay (including but not limited to FACE, or anthranilic acid labeling HPLC, HPLC, ELISA or SDS-PAGE).

Figure 6:
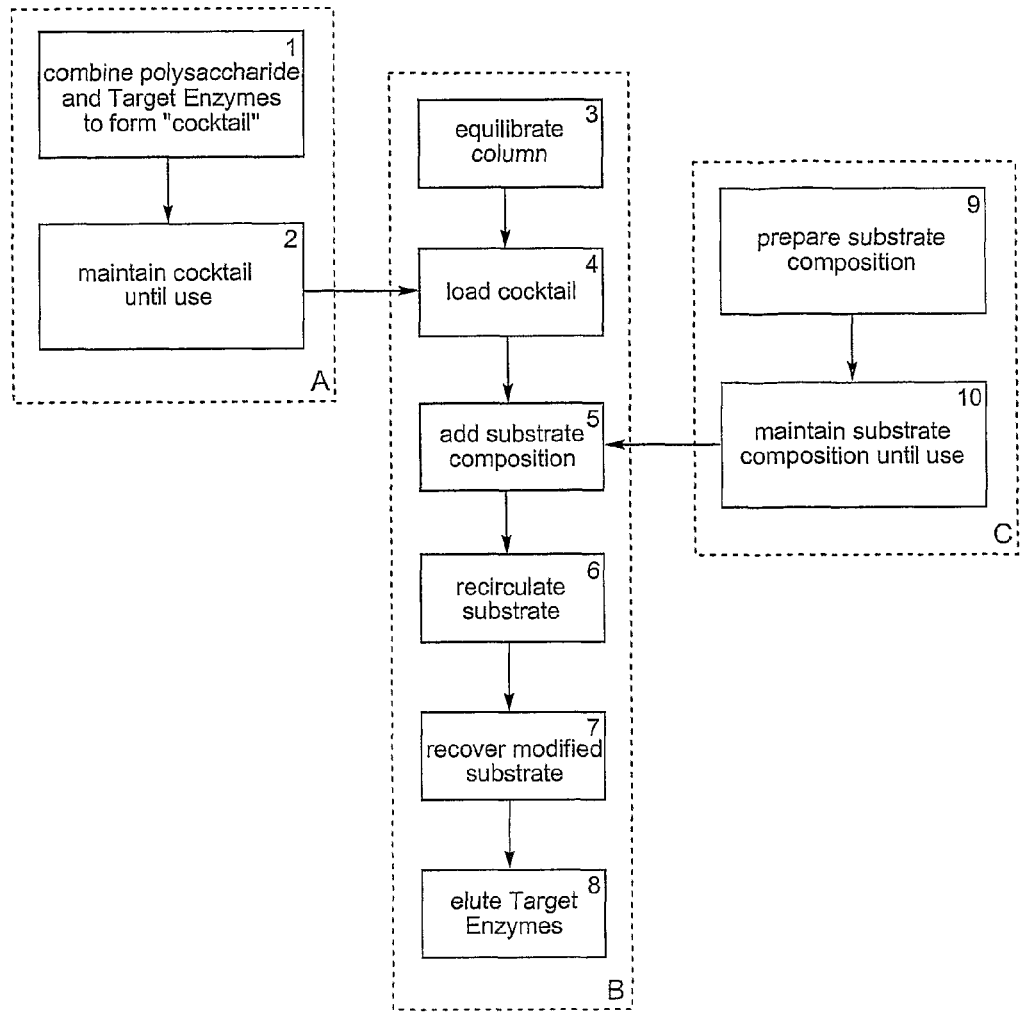
FIG. 6 is a flow-chart illustrating one embodiment of the methods of the invention, wherein the Target Enzyme is immobilized on a solid support and the substrate is in solution.

Another embodiment of a method of the invention is depicted in FIG. 6. In this embodiment, the activity of a Target Enzyme immobilized on a solid support, such as a resin packed within a column, is promoted by a polysaccharide in the presence of a substrate in solution. The preparation of a Target Enzyme cocktail (process A) includes combining the polysaccharide with the Target Enzyme (step 1) to prepare a "cocktail," and maintaining the cocktail until use (step 2). A composition comprising the substrate is prepared (process C, step 9) and maintained until use (step 10). Optionally, a column packed with a suitable resin (e.g., a resin capable of retaining the Target Enzyme(s) is equilibrated (process B, step 3). The Target Enzyme cocktail is loaded onto the column (step 4). The substrate composition is then added to the column (step 5), and optionally recirculated through the column (step 6), allowing the Target Enzyme to modify the substrate. The substrate composition may be recirculated through the column for a period of time including but not limited to from about: 1 to 240 hours, 1 to 40 hours, 5 to 35 hours, 10 to 30 hours, 15 to 30 hours, or 19 to 25 hours. Alternatively, depending upon the kinetics of the enzymatic reaction, the substrate may be recirculated through the column for a period of time including but not limited to from about: 1 to 48 hours, 1 to 24 hours, 1 to 12 hours, 1 to 6 hours, and 1 to 3 hours. Alternatively, the substrate may be recirculated through the column for a period of time less than about 1 hour. Once a desired level of modification is achieved, the modified substrate is recovered (step 7). Optionally, the Target Enzyme may also be recovered (step 8). Other variations of this embodiment are also within the scope of the invention. For example, Process A may be eliminated from the embodiment shown in FIG. 6 and the polysaccharide may be added directly to the column either before, after or at the same time the substrate is added to the column. In other embodiments, the solid support or resin is not in the form of a column, but is e.g., in the form of a slurry, batch or other form.

In the methods of the present invention, the order in which the Target Enzyme, the polysaccharide, and optionally, the substrate are combined is not critical. Therefore, in still further embodiments of the invention, the Target Enzyme, the polysaccharide, and the substrate composition may be added together or the polysaccharide may be added to the substrate composition prior to the addition of the Target Enzyme.

Accordingly, one advantage of the methods described herein is that it allows use of a decreased amount of the Target Enzyme as compared to the amount required if the activity had not been promoted.

The present invention further provides methods of promoting the enzymatic activity of a Target Enzyme (e.g., in liquid milieu), the method comprising:

(a) combining a Target Enzyme with a non-naturally occurring polysaccharide and optionally a substrate of the Target Enzyme; and (b) maintaining the combination prepared in step (a), without freezing for a period of time: (i) sufficient to promote Target Enzyme activity compared to a suitable control, such as a Target Enzyme activity in the absence of the polysaccharide (compared to the activity of a Target Enzyme that has not been combined with the non-naturally occurring polysaccharide); and/or (ii) sufficient for a substantial loss of Target Enzyme activity in the absence of the polysaccharide. As noted herein, enzymatic activity and enzymatic reactions can be measured by standard methods (see, e.g., Eisenthal et al., *Enzyme Assays: A Practical Approach*, Oxford University Press: New York, 2002 and descriptions in the Examples). The methods of the invention may further comprise:

(c) allowing the Target Enzyme to modify the substrate, thereby producing a modified substrate; and (d) recovering the modified substrate.

The invention is also directed to compositions comprising modified substrates or Target Enzymes produced by the methods described herein.

The combinations may be maintained in step (b) for at least about: 1, 2, 3, 4, 5, 6, 10, 15, 20, 22, 24 or 48 hours, or at least about: 1, 2, 3, 4, 5, 6, 7, 8, 9, 10, 11, 15, 20, 30, 40, 50, or 60 days but less than 90 days. For example, the combinations may be maintained for from about: 1 to 40 hours, 5 to 35 hours, 10 to 30 hours, 15 to 30 hours, or 19 to 25 hours. In some aspects, the combination may be maintained for from about: 1 to 90 days, 1 to 45 days, 46 to 90 days, 2 to 60 days, 2 to 30 days, 2 to 15 days, or 2 to 7 days.

As noted above, the Target Enzyme of the methods herein may be any enzyme, for example, an oligosaccharide/polysaccharide enzyme including but not limited to those listed in Table 1, a protein enzyme including but not limited to those listed in Table 2, or a polynucleotide enzyme including but not limited to those listed in Table 3, a lipase, a lysosomal hydrolase, including but not limited to those listed in Table 4 or a small molecule enzyme.

As one of skill in the art will appreciate, cognate substrates for particular Target Enzymes are well known in the art. Generally, without limitation, a substrate may be a protein, a peptide, a nucleotide, a lipid, an oligonucleotide or a small molecule. For example, in some embodiments, the substrate is a therapeutic protein. For example, in some preferred embodiments, the substrate may be an ERT enzyme including, but not limited those listed in Table 4. In one preferred embodiment, (1) the Target Enzymes are sialidase, β-galactosidase, and β-N-acetylhexosaminidase; (2) the starch is HES; and (3) the substrate is β-glucocerebrosidase.

The invention further provides methods of promoting the enzymatic activity of enzymes that modify oligosaccharides. For example, in one embodiment, the method comprises combining one or more enzymes (e.g., oligosaccharide modification enzymes) that modify β-glucocerebrosidase with about 3% to about 7% HES, thereby producing a combination. The combination is maintained under conditions in which the activity of the one or more enzymes is promoted (enhanced) when compared to a suitable control (e.g., compared to the activity of the one or more oligosaccharide modification enzymes that has not been combined with about 3% to about 7% HES). The extent of the modification of such oligosaccharides can be measured by standard methods such as anthranilic acid labeling HPLC methods or fluorophore-assisted carbohydrate electrophoresis (FACE) (see, e.g., Eisenthal et al., *Enzyme Assays: A Practical Approach*, Oxford University Press: New York, 2002 and descriptions in the Examples).

In a specific embodiment, the method comprises:
(a) combining β-glucocerebrosidase with one or more oligosaccharide modification enzymes and with about 3% to about 7% HES, thereby producing a combination; and
(b) maintaining the combination under conditions in which the oligosaccharide/polysaccharide enzymes modify the β-glucocerebrosidase in the presence of the HES, thereby producing modified β-glucocerebrosidase. The method can further comprise recovering the modified β-glucocerebrosidase.

In some embodiments, the invention provides a method of promoting the enzymatic activity of a Target Enzyme during manufacture of a Target Enzyme and/or substrate, including but not limited to an oligosaccharide/polysaccharide enzyme or a lysosomal hydrolase.

The invention further provides a method of promoting the enzymatic activity of a Target Enzyme during one or more purification steps of the Target Enzyme and/or substrate. A number of purification steps are known in the art (see, e.g., Scopes *Protein Purification: Principles and Practice*, 3$^{rd}$ ed., Springer-Verlag: New York, 1994; Abelson et al., *Guide to Protein Purification*, Academic Press: New York, 1990; Roe *Protein Purification Techniques: A Practical Approach*, 2nd ed., Oxford University Press: New York, 2001). Purity may be assessed by any suitable method, including but not limited to SDS-PAGE, capillary electrophoresis or HPLC.

In a particular embodiment, the invention is directed to a method of promoting the enzymatic activity of one or more enzymes (e.g., oligosaccharide/polysaccharide enzymes) that modify β-glucocerebrosidase. For example, the methods described herein can be used to promote the enzymatic activity of sialidase, β-galactosidase and/or β-hexosaminidase during purification of β-glucocerebrosidase (e.g., from recombinant cells). In this embodiment, the method comprises combining β-glucocerebrosidase; an oligosaccharide/polysaccharide enzyme selected from the group consisting of: sialidase, β-galactosidase, β-hexosaminidase and a combination thereof; and about 3% to about 7% HES, thereby producing a combination. The combination is maintained under conditions in which the enzymatic activity of sialidase, β-galactosidase and/or β-hexosaminidase is promoted (e.g., compared to a suitable control) and in which the enzymes modify the β-glucocerebrosidase in the presence of the HES. Modified β-glucocerebrosidase is thereby produced, and the method can further comprise recovering the modified β-glucocerebrosidase.

The methods described herein can also be used to stabilize the Target Enzyme such that it can act on a substrate, comprising combining the substrate, a Target Enzyme that remodels the substrate and about 0.1% to about 55% w/v of a non-naturally occurring polysaccharide, thereby producing a combination. The combination is maintained under conditions in which enzymatic alteration of the substrate by the Target Enzyme occurs in the presence of the non-naturally-occurring polysaccharide. In a particular embodiment, the invention provides a method of enzymatically altering an oligosaccharide of a substrate (e.g., β-glucocerebrosidase) by an oligosaccharide/polysaccharide enzyme (e.g., sialidase, β-galactosidase and/or β-hexosaminidase) comprising combining the substrate, the enzyme and about 0.1% to about 15% w/v of a non-naturally occurring polysaccharide, thereby producing a combination. The combination is maintained under conditions in which remodeling of the substrate by the enzyme occurs in the presence of the non-naturally-occurring polysaccharide.

Additional Compositions

The present invention also provides a composition comprising (a) a Target Enzyme selected from the group consisting of an oligosaccharide/polysaccharide enzyme, a protein enzyme, a polynucleotide enzyme, a lipase, a kinase and a lysosomal hydrolase, and (b) a non-naturally occurring polysaccharide, wherein the composition comprises from about 0.01% to 55% w/v, about 0.1% to 50% w/v, about 1% to 50% w/v, about 5% to 40% w/v, about 10% to 40% w/v, about 15% to 35% w/v, about 20% to 30% w/v, about 0.01 to about 15% w/v, about 0.1% to 15% w/v, about 1% to 10% w/v, about 5% to 15% w/v, about 3% to 7% w/v, or about 4% to 6% of the polysaccharide. In some embodiments, the Target Enzyme is itself a therapeutic protein.

The present invention further provides a composition comprising (a) a purified Target Enzyme, (b) a non-naturally occurring polysaccharide, and (c) a substrate of the enzyme, wherein the composition comprises from about 0.01% to 55% w/v, about 0.1% to 50% w/v, about 1% to 50% w/v, about 5% to 40% w/v, about 10% to 40% w/v, about 15% to 35% w/v, about 20% to 30% w/v, about 0.01% to about 15% w/v, about 0.1% to 15% w/v, about 1% to 10% w/v, about 5% to 15% w/v, about 3% to 7% w/v, or about 4% to 6% w/v of the polysaccharide.

The present invention further provides a composition comprising (a) one or more oligosaccharide/polysaccharide enzymes and (b) from about 0.01% to 55% w/v, about 0.1% to 50% w/v, about 1% to 50% w/v, about 5% to 40% w/v, about 10% to 40% w/v, about 15% to 35% w/v, about 20% to 30% w/v, about 0.01% to about 15% w/v, about 0.1% to 15% w/v, about 1% to 10% w/v, about 5% to 15% w/v, about 3% to 7% w/v, or about 4% to 6% w/v HES. The oligosaccharide/polysaccharide enzyme is maintained in the presence of HES and the activity of that oligosaccharide/polysaccharide enzyme is measured over time by withdrawing samples and determining enzymatic activity toward an appropriate substrate. In another embodiment, the invention provides a composition comprising (a) one or more oligosaccharide/polysaccharide enzymes, (b) from about 0.01% to 55% w/v, about 0.1% to 50% w/v, about 1% to 50% w/v, about 5% to 40% w/v, about 10% to 40% w/v, about 15% to 35% w/v, about 20% to 30% w/v, about 0.01% to about 15% w/v, about 0.1% to 15% w/v, about 1% to 10% w/v, about 5% to 15% w/v, about 3% to 7% w/v, or about 4% to 6% w/v HES, and (c) a substrate of the enzyme.

Additional Illustrative, nonlimiting combinations are show in Table 5.

TABLE 5

Illustrative Combinations

| Target Enzyme | Polysaccharide | Substrate Present |
|---|---|---|
| Any | A chemically modified starch or Ficoll ® | Yes |
| Any | Hydroxyalkyl starch | Yes |
| Any | HES | Yes |

TABLE 5-continued

Illustrative Combinations

| Target Enzyme | Polysaccharide | Substrate Present |
|---|---|---|
| A sugar-modifying enzyme | Any | Yes |
| A sugar-modifying enzyme | A chemically modified starch or Ficoll ® | Yes |
| A sugar-modifying enzyme | Hydroxyalkyl starch | Yes |
| A sugar-modifying enzyme | HES | Yes |
| Sialidase, β-galactosidase, or β-N-acetylhexosaminidase | Any | Yes |
| Sialidase, β-galactosidase, or β-N-acetylhexosaminidase | A chemically modified starch or Ficoll ® | Yes |
| Sialidase, β-galactosidase, or β-N-acetylhexosaminidase | Hydroxyalkyl starch | Yes |
| Sialidase, β-galactosidase, or β-N-acetylhexosaminidase | HES | Yes |
| A lysosomal hydrolase | Any | Yes |
| A lysosomal hydrolase | A chemically modified starch or Ficoll ® | Yes |
| A lysosomal hydrolase | Hydroxyalkyl starch | Yes |
| A lysosomal hydrolase | HES | Yes |
| β-Glucocerebrosidase | Any | Yes |
| β-Glucocerebrosidase | A chemically modified starch or Ficoll ® | Yes |
| β-Glucocerebrosidase | Hydroxyalkyl starch | Yes |
| β-Glucocerebrosidase | HES | Yes |
| α-glucosidase | Any | Yes |
| α-glucosidase | A chemically modified starch or Ficoll ® | Yes |
| α-glucosidase | Hydroxyalkyl starch | Yes |
| α-glucosidase | HES | Yes |
| Agalsidase beta | Any | Yes |
| Agalsidase beta | A chemically modified starch or Ficoll ® | Yes |
| Agalsidase beta | Hydroxyalkyl starch | Yes |
| Agalsidase beta | HES | Yes |
| Any | A chemically modified starch or Ficoll ® | No |
| Any | Hydroxyalkyl starch | No |
| Any | HES | No |
| A sugar-modifying enzyme | Any | No |
| A sugar-modifying enzyme | A chemically modified starch or Ficoll ® | No |
| A sugar-modifying enzyme | Hydroxyalkyl starch | No |
| A sugar-modifying enzyme | HES | No |
| Sialidase, β-galactosidase, or β-N-acetylhexosaminidase | Any | No |
| Sialidase, β-galactosidase, or β-N-acetylhexosaminidase | A chemically modified starch or Ficoll ® | No |
| Sialidase, β-galactosidase, or β-N-acetylhexosaminidase | Hydroxyalkyl starch | No |
| Sialidase, β-galactosidase, or β-N-acetylhexosaminidase | HES | No |
| A lysosomal hydrolase | Any | No |
| A lysosomal hydrolase | A chemically modified starch or Ficoll ® | No |
| A lysosomal hydrolase | Hydroxyalkyl starch | No |
| A lysosomal hydrolase | HES | No |
| β-Glucocerebrosidase | Any | No |
| β-Glucocerebrosidase | A chemically modified starch or Ficoll ® | No |
| β-Glucocerebrosidase | Hydroxyalkyl starch | No |
| β-Glucocerebrosidase | HES | No |
| α-glucosidase | Any | No |
| α-glucosidase | A chemically modified starch or Ficoll ® | No |
| α-glucosidase | Hydroxyalkyl starch | No |
| α-glucosidase | HES | No |
| Agalsidase beta | Any | No |
| Agalsidase beta | A chemically modified starch or Ficoll ® | No |
| Agalsidase beta | Hydroxyalkyl starch | No |
| Agalsidase beta | HES | No |

The invention further provides a pharmaceutical composition comprising a Target Enzyme and a non-naturally occurring polysaccharide wherein the composition comprises from about 0.01% to about 55% w/v of the polysaccharide. In another embodiment, the pharmaceutical composition comprises substrates which themselves may be enzymes, including lysosomal hydrolases produced according to such methods, and methods of using the same. In illustrative embodiments, the invention provides pharmaceutical compositions, comprising lysosomal hydrolases, including, e.g., β-glucocerebrosidase, produced according to the methods of the inventions. Acceptable pharmaceutical formulations and excipients are known (see, e.g., 2005 *Physicians' Desk Reference®*, Thomson Healthcare: Montvale, N.J., 2004; *Remington: The Science and Practice of Pharmacy*, 20th ed., Gennado et al., Eds. Lippincott Williams & Wilkins: Philadelphia, Pa., 2000; *Handbook of Pharmaceutical Excipients*, 5$^{th}$ ed., Rowe, R., et al., 2005; Kibbe, A. H. (ed.), *Handbook of Pharmaceutical Excipients*, 3$^{rd}$ ed., Washington, D.C., American Pharmaceutical Association; M. F. Powell, et al., *PDA Journal of Pharm. Sci. Tech.*, 52:238-311 (1998); S, Neema, et al., Encyclopedia of Pharmaceutical Technology; J. Swarbick and J. C. Boylan eds., M. Dekker (2002), which are incorporated herein by reference.).

The pharmaceutical compositions of the invention optionally include one or more pharmaceutically acceptable carriers, diluents, excipients, fillers and/or stabilizers (e.g., lactose, cellulose, dextrose), which are "acceptable" in the sense of being compatible with other ingredients of the pharmaceutical compositions and not deleterious to the composition or the recipient of the composition. The pharmaceutical compositions can conveniently be presented in a unit dosage form and can be prepared by any suitable method known to the skilled artisan. In general, the pharmaceutical compositions are prepared by bringing into association the Target Enzyme, the non-naturally occurring polysaccharide and/or the substrate with the carrier, diluent, excipient, filler and/or stabilizer, and then, if necessary, dividing the product into unit dosages thereof.

The pharmaceutical compositions can be formulated, for example, as a sachet, slurry, troche, elixir, suspension, liquid or tablet. In particular embodiments, the pharmaceutical compositions are formulated for injection. For example, the pharmaceutical compositions are formulated for liquid injectables (vial, prefilled syringe), lyophilized injectables (vial, dual chamber syringe), inhalable administration (microparticles, nebulized), sustained release oral and injectable formulations, eye drops, and/or intranasal administration (liquid). In one embodiment, the pharmaceutical composition comprises the Target Enzyme and non-naturally occurring polysaccharide in a liquid carrier (e.g., water). The pharmaceutical composition can optionally comprise a pharmaceutically acceptable preservative (e.g., benzyl alcohol; phenol). In a particular embodiment, the pharmaceutical composition comprises a Target Enzyme that has been solubilized or resolubilized (such as resolubilization of a lyophilized product) in a liquid comprising a non-naturally occurring polysaccharide.

The invention further provides methods of treating a lysosomal storage disorder, such as an LSD listed in Table 4 (e.g., Gaucher Disease), comprising administering to a subject in need thereof (e.g., a mammal, such as a human), a pharmaceutical composition of the invention. Administration is not limited to any particular delivery system and may include, without limitation, intravenous, parenteral (including subcutaneous, intramedullary, intraarticular, intramuscular, or intraperitoneal injection), transdermal, or oral (for example, in capsules, suspensions, or tablets and sustained delivery means and devices). Administration to an individual may occur in a single dose or in repeat administrations, and in any of a variety of physiologically acceptable salt forms, and/or with an acceptable pharmaceutical carrier and/or additive as part of a pharmaceutical composition (described herein).

The compositions herein may be administered as a dose of approximately from 1 μg/kg to 80 mg/kg of active ingredient, depending on the severity of the symptoms and the progression of the disease. Alternatively, a dose of approximately from 0.01 Unit per kilogram of patient body weight (U/kg) to 1000 U/kg is administered. Any means of administration known in the art may be used to administer the compositions of the invention. Most commonly, proteinaceous compounds are administered in an outpatient setting by daily, weekly, biweekly, monthly, or bimonthly administration. Certain compositions may be administered only a few times or only once. The appropriate therapeutically effective dose of a compound is approximately from about 1 μg/kg to 80 mg/kg, from about 1 μg/kg to 25 mg/kg from about 1 μg/kg to 10 mg/kg, from about 1 μg/kg to 1 mg/kg, from about 10 μg/kg to 1 mg/kg, from about 10 μg/kg to 100 μg/kg, from about 100 μg to 1 mg/kg, or from about 500 μg/kg to 15 mg/kg. Alternatively, appropriate therapeutically effective dose of an enzyme is approximately: from about 0.1 U/kg to 200 U/kg, from about 5 U/kg to 300 U/kg, from about 10 U/kg to 100 U/kg, from about 100 U/kg to 500 U/kg, from about 5 U/kg to 50 U/kg, from about 500 U/kg to 2000 U/kg, or from about 1000U/kg to 2500U/kg. Additionally, specific dosages are indicated in the *Physicians' Desk Reference®*.

For example, in one embodiment, β-glucocerebrosidase produced by the methods of the invention may be administered to a subject by intravenous (IV) infusion. For example, initial dosing regimens, which can be adjusted by a clinician on the basis of disease severity, can comprise single or multiple doses per week of about 1 U/kg to 5U/kg body weight or approximately biweekly doses of about 30-100 U/kg body weight, where a unit (U) of GCR is defined as the amount of GCR that catalyzes the hydrolysis of 1 μmol of p-nitrophenyl-β-D-glucopyranoside per minute at 37° C. IV infusion is generally over the course of 1-2 hours.

For example, in another embodiment, α-galactosidase produced by the methods of the invention may be administered to a subject by intravenous (IV) infusion. For example, initial dosing regimens, which can be adjusted by a clinician on the basis of disease severity, can comprise single or multiple doses per week of about 0.3-3.0 mg/kg. IV infusion is generally over the course of 1-2 hours. In relation to α-galactosidase, a unit (U) defined as the amount of enzyme that catalyzes the hydrolysis of 1 μmol of p-nitrophenyl-β-D-galactopyranoside per minute at 37° C.

In yet another embodiment, α-glucosidase produced by the methods of the invention may be administered to a subject by intravenous (IV) infusion. For example, initial dosing regimens, which can be adjusted by a clinician on the basis of disease severity, can comprise single or multiple doses per week of about 20 mg/kg to about 40 mg/kg on a bimonthly delivery. IV infusion is generally over the course of 4-7 hours. In relation to α-glucosidase, a unit (U) is defined as the amount of enzyme that catalyzes the hydrolysis of 1 μmol of p-nitrophenyl-β-D-galactopyranoside per minute at 37° C.

Assays to Evaluate Enzymatic Activity of Target Enzyme

The enzymatic activity of a Target Enzyme can be assessed by an appropriate assay determined by one skilled in the art (see, e.g., Eisenthal et al., *Enzyme Assays: A Practical Approach*, Oxford University Press: New York, 2002; Freifelder, D., *Physical* Biochemistry: *Applications to Biochemistry and Molecular Biology*, $2^{nd}$ Ed., W.H. Freeman & Co., New York, 1982 and descriptions in the Examples).

For example, the modification state of a substrate or the extent of an enzymatic reaction containing a Target Enzyme or the activity of a Target Enzyme may be measured by assays known in the art, including but not limited to electrophoresis, chromatography, immunological methods, hydrodynamic methods, spectroscopic methods or other method), see e.g., Freifelder, D., Physical Biochemistry: Applications to Biochemistry and Molecular Biology, $2^{nd}$ Ed., W.H. Freeman & Co., New York, 1982; see also, Eisenthal et al., *Enzyme Assays: A Practical Approach*, Oxford University Press: New York, 2002. In other embodiments, the extent of modification may be determined during or after the process by, e.g., sampling the reaction mixture and examining the modification state of the substrate using an appropriate analytical method (including but not limited to FACE, HPLC or SDS-PAGE, or an assay noted above). Selection of the appropriate assay to be used in conjunction particular Target Enzyme may also be determined by one of ordinary skill in the art through simple and routine experimentation.

EXEMPLIFICATION

General Information

In the Examples below, unless otherwise indicated, hydroxyethyl starch (HES) from B. Braun was used. The HES from B. Braun has an indicated average molecular weight (AMW) in the range of 450-700 kDa, with a (hydroxyethyl) molar substitution (MS) of 0.70-0.80. The comparability of two additional sources of HES (obtained from Ajinomoto and Fresenius Kabi) to promote Target Enzyme activity is shown in Example 11.

Several lots of Target Enzymes are used in Examples 1-9. The activity of each of the stock solutions of the three Target Enzymes (sialidase, β-galactosidase, and β-hexosaminidase) was measured, as described below. The Units (U) of each of the three Target Enzymes added for β-glucocerebrosidase (GCR) oligosaccharide/polysaccharide reaction was calculated from that measurement. In these Examples, GCR serves as an enzymatic substrate for the oligosaccharide/polysaccharide enzymes (i.e., Target Enzymes): sialidase, β-galactosidase, and β-hexosaminidase.

Face Assay

The fluorophore-assisted carbohydrate electrophoresis (FACE) assay (see, e.g., Jackson, *Biochem. Soc. Trans.* 21:121-5 (1993); Hu, *J. Chromatogr. A* 705:89-103 (1995); Friedman et al., *Anal. Biochem.* 228:221-225 (1995); Starr et al., *J. Chromatogr. A* 720:295-321 (1996)) is a standard assay for characterizing and measuring oligosaccharides. It can also be used to characterize monosaccharides (Gao et al., *Glycobiology* 13:1G-3G (2003)).

The FACE assay is a preferred method of monitoring the enzymatic activity of the oligosaccharide/polysaccharide enzymes (such as the Target Enzymes in certain Examples herein) by determining the extent of modification of a substrate (including, but not limited to, a protein, glycoprotein or oligosaccharide) of a Target Enzyme(s). Using a FACE assay, a higher FACE number is indicative of a greater degree of modification and a greater degree of Target Enzyme(s) activity. The FACE assays are known in the art.

Briefly, when the oligosaccharide being assayed is from a glycoprotein, the oligosaccharide is first cleaved from the protein (e.g., by N-glycanase treatment to release an intact N-linked oligosaccharide, by O-glycanase treatment to release an intact O-linked oligosaccharide, or by endo-β-N-acetylglucosaminidase H treatment to release an intact high-mannose-type N-linked oligosaccharide (Turner et al. Glycosylation and Glycosylphosphatidylinositol Membrane Anchors. In Regulatory *Protein Modification*, Hemmings, Ed., Humana Press: Totawa, N.J., 1997).

The intact oligosaccharide chains are next labeled with a fluorophore, such as disodium 8-amino-naphthalene-1,3,6-trisulfonate (ANTS),2-aminoacridone (AMAC), potassium 7-amino-1,3,-naphthalene disulfonate (ANDA) and sodium 4-amino-naphthalene sulfonate (ANSA), by reductive amination of a primary amine of the fluorophore with the reducing end of an oligosaccharide in the presence of sodium cyanoborohydride. The fluorophore may be negatively charged (for example, due to sulfation, as in the non-limiting examples, using ANTS, ANDA, ANSA).

The fluorophore-labeled oligosaccharides are then separated by electrophoresis on a high percentage polyacrylamide gel. The charge necessary for migration in an electric field is provided by the intrinsic chemical structure of the oligosaccharide (as in, for example, oligosaccharides comprising sialic acid or phosphorylated or sulfated monosaccharides) or by the fluorophore.

The resulting gel is next imaged using a long-wavelength UV light box, and the various bands are identified and their fluorescence quantified. Oligosaccharides can be quantified at concentrations as dilute as the low picolmole range by this method (Starr et al., *J. Chromatogr. A* 720:295-321 (1996)).

In the Examples herein, when the Target Enzymes were sialidase, β-galactosidase, and β-hexosaminidase, a FACE assay was used to determine the percentage of modified oligosaccharide species in the GCR substrate. Specifically, GCR was treated with N-glycanase (approximately 8 U of N-glycanase per 40 μg GCR) to release intact N-linked oligosaccharide chains. The released oligosaccharides were then labeled with the fluorophore: ANTS (8-aminonapthalene-1, 3,6-trisulfonic acid and separated on oligosaccharide profiling gel (Glyko®/Prozyme®, San Leandro, Calif.) as per the manufacturers instructions. A dextran reference ladder standard (Glyko®)/Prozyme®, San Leandro, Calif.) was also run on the gel along with reference oligosaccharides, GlcNAc$_2$(+Fuc)Man$_3$ and GlcNAc$_2$(-Fuc)Man$_3$, Glyko®/Prozyme®, San Leandro, Calif.). Bands on the gel were then quantified by scanning the gel for fluorescence using a SE2000 imager system with fluorescence imaging software (Glyko®/Prozyme®, San Leandro, Calif.).

The ratio (%) of the fluorescent intensity of the bands representing two core structures, GlcNAc$_2$(Fuc)Man$_3$ and GlcNAc$_2$Man$_3$ (core structures), to the total intensity of bands with mobility ≤GlcNac$_2$Man$_3$ in a given lane provided the percentage of modified GCR. Since GCR acts as a substrate for the three Target Enzymes, sialidase, β-galactosidase, and β-hexosaminidase, the FACE results correlate to the activity of the Target Enzymes against GCR. For GCR, the FACE values can range from about 0 to about 100%, about 3% to about 90% and about 5% to about 85%.

Measuring Target Enzyme Activity & Determining Units/mL of Target Enzyme

The enzymatic activity of a Target Enzyme can be assessed by an appropriate assay determined by one skilled in the art (see, e.g., Eisenthal et al., *Enzyme Assays: A Practical Approach*, Oxford University Press: New York, 2002 and descriptions in the Examples).

The enzymatic activity of the three Target Enzymes employed in the Examples presented below are described in the following six paragraphs.

β-Glucocerebrosidase (GCR) Activity Assay:

β-glucocerebrosidase (β-D-glucosidase) activity of stock solutions was assayed by measuring the rate of hydrolysis of the synthetic substrate p-nitrophenyl-β-D-glucopyranoside (pNP-βGlc) (Sigma Aldrich, St. Louis, Mo.) to p-nitrophenol (pNP). In these assays, 80 μl of pNP-βGlc at 10 mM was added to 20 μl of β-glucosidase sample, and the sample was incubated at 37° C. for fifteen minutes. After the reaction was quenched with 800 μl of 0.1 M glycine, pH 10.5, the absorbance at 400 nm of the sample was measured. The activity of the β-glucosidase sample was calculated according to the following equation:

$$\text{Units/mL} = \frac{(A_{400}) * (\text{dilution factor of sample}) * (\text{total assay sample volume})}{\varepsilon * (\text{time}) * (\text{light path length}) * (\text{sample volume})}$$

wherein $A_{400}$ is the absorbance of the sample at 400 nm, ε is the molar extinction coefficient of pNP at 400 nm, time is measured in minutes, the light pathlength is one cm, and sample volume is measured in mL.

α-Glucosidase Activity Assay:

α-glucosidase (α-D-glucosidase) activity of stock solutions was assayed by measuring the rate of hydrolysis of the synthetic substrate p-nitrophenyl-α-D-glucopyranoside (pNP-αGlc) (Sigma Aldrich, St. Louis, Mo.) to p-nitrophenol (pNP). In these assays, 225 µl of pNP-αGlc at 40 mM was added to 25 µl of α-glucosidase sample, and the sample was incubated at 37° C. for fifteen minutes. After the reaction was quenched with 0.25 ml of 0.3 M glycine, pH 10.6, the absorbance at 400 nm of the sample was measured. The activity of the α-glucosidase sample was calculated according to the following equation:

$$\text{Units/mL} = \frac{(A_{400}) * (\text{dilution factor of sample}) * (\text{total assay sample volume})}{\varepsilon * (\text{time}) * (\text{light path length}) * (\text{sample volume})}$$

wherein $A_{400}$ is the absorbance of the sample at 400 nm, $\varepsilon$ is the molar extinction coefficient of pNP at 400 nm, time is measured in minutes, the light pathlength is one cm, and sample volume is measured in mL.

α-Galactosidase Activity Assay:

α-galactosidase (α-D-galactosidase) activity of stock solutions was assayed by measuring the rate of hydrolysis of the synthetic substrate p-nitrophenyl-α-D-galactopyranoside (pNP-αGal) (Sigma Aldrich, St. Louis, Mo.) to p-nitrophenol (pNP). In these assays, 75 µl of pNP-αGal at 30 mM was added to 175 µl of α-galactosidase sample, and the sample was incubated at 37° C. for ten minutes. After the reaction was quenched with 0.25 ml of 0.5 M sodium borate, pH 9.0, the absorbance at 405 nm of the sample was measured. The activity of the α-galactosidase sample was calculated according to the following equation:

$$\text{Units/mL} = \frac{(\Delta OD\ \text{Sample}) * (\text{dilution factor}) * (pNP\ Std\ conc.) * (\text{total assay volume})}{(\text{time}) * (\Delta OD\ Std) * (\text{sample volume})}$$

wherein $\Delta OD$ is the difference in absorbance at 405 nm of the sample (or standard (Std)) and blank, time is measured in minutes, and sample volume is measured in mL.

Sialidase (neuraminidase) Activity Assay:

Sialidase (neuraminidase) activity of stock solutions was determined by measuring the rate of the sialidase-catalyzed hydrolysis of the synthetic substrate 4-methylumbelliferyl-N-acetylneuraminic acid (4MU-NANA) (Sigma Aldrich Company, St. Louis, Mo.) to 4-methylumbelliferone (4MU). In these assays, 100 µl of 4MU-NANA at 5-10 uM was added to 10 µl of purified sialidase. After fifteen minutes the reaction was quenched by adding 5 ml of 0.1 M glycine, pH 10.5, and 1.5 ml of the sample was analyzed with a fluorometer (excitation 360 nm, emission 450 nm). The results were extrapolated onto a standard curve generated with 4MU solution to determine the quantity of 4MU released during the incubation. The activity was calculated according to the following equation:

$$\text{Units/mL} = \frac{(4MU\ \text{released}) * (\text{dilution factor of sample})}{(\text{sample volume}) * (\text{time}) * 1000}$$

wherein the amount of 4MU released is measured in nmol, the sample volume is measured in milliliters (mL), and time is measured in minutes. Thus, for example, using the above calculation, if an enzyme stock solution is determined to have an activity of 1000 Units/mL, and one desired to use 2000 Units of enzyme in an enzymatic reaction, such reaction would require 2 mL of such stock solution.

β-Galactosidase Activity Assay:

β-galactosidase (β-D-galactosidase) activity of stock solutions was assayed by measuring the rate of hydrolysis of the synthetic substrate o-nitrophenyl-β-D-galactopyranoside (oNPGal) (Sigma Aldrich, St. Louis, Mo.) to o-nitrophenol (oNP). In these assays, 400 µl of oNPGal at 15 mM was added to 100 µl of β-galactosidase sample, and the sample was incubated at 37° C. for fifteen minutes. The reaction was then quenched by the addition of 2.5 ml of 0.1 M glycine, pH 10.5, and the absorbance of the sample at 430 nm was measured. The activity of the β-galactosidase sample was calculated according to the following equation:

$$\text{Units/mL} = \frac{(A_{430}) * (\text{dilution factor of sample}) * (\text{total assay sample volume})}{\varepsilon * (\text{time}) * (\text{light path length}) * (\text{sample volume})}$$

wherein $A_{430}$ is the absorbance of the sample at 430 nm, $\varepsilon$ is the molar extinction coefficient of oNP at 430 nm, time is measured in minutes, the light path length is one cm, and sample volume is measured in mL.

β-Hexosaminidase Activity Assay:

β-Hexosaminidase activity (β-N-acetylglucosaminidase) of stock solutions was assayed by measuring the rate of β-hexosaminidase-catalyzed hydrolysis of the synthetic substrate p-nitrophenyl-β-D-N-acetylglucosaminide (pNPGlcNAc) (Sigma Chemical, St Louis, Mo.) to p-nitrophenol (pNP). In these assays, 400 µl of pNPGlcNAc at 4 mM was added to 100 µl of β-hexosaminidase sample. The sample was incubated at 37° C. for fifteen minutes. After the reaction was quenched with 2.5 ml of 0.1 M glycine, pH 10.5, the absorbance at 400 nm of the sample was measured. The activity of the β-hexosaminidase sample was calculated according to the following equation:

$$\text{Units/mL} = \frac{(A_{400}) * (\text{dilution factor of sample}) * (\text{total assay sample volume})}{\varepsilon * (\text{time}) * (\text{light path length}) * (\text{sample volume})}$$

wherein $A_{400}$ is the absorbance of the sample at 400 nm, $\varepsilon$ is the molar extinction coefficient of pNP at 400 nm, time is measured in minutes, the light path length is one cm, and sample volume is measured in mL.

As used herein, "sv" means the system volume used (e.g., in the case of a column, sv refers to the resin bed volume plus the volume contained in the associated column piping; in the case of a batch, the system volume refers to the total volume of the batch). "U/L sv" refers to the units of enzyme per liter of system volume. "% w/L sv" refers to the percent weight per liter of system volume.

Example 1

Effect of HES on GCR Stability

Figure 7:
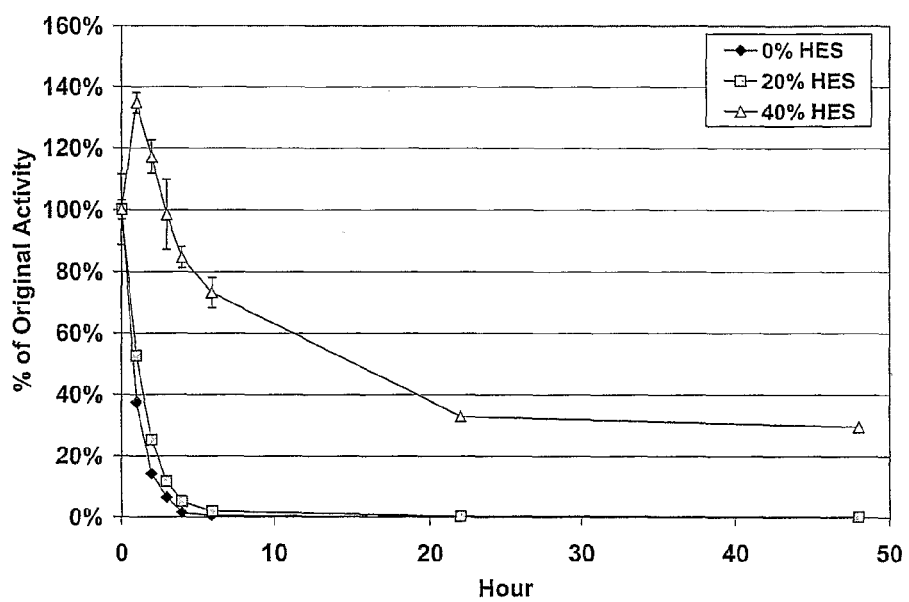
FIG. 7 is a graph of hour versus % of original activity illustrating the effect of HES on promoting rGCR stability.

A study was conducted to evaluate the effect of HES on the Target Enzyme β-glucocerebrosidase under conditions intended to promote a loss of Target Enzyme enzymatic activity in the absence of a stabilizer, such as HES (i.e., stressed enzyme). Specifically, GCR at a concentration of 4 mg/ml in 50 mM Sodium Phosphate, pH 7.5 was prepared into solutions of 0%, 10% or 40% HES by adding appropriate volumes of a 50% HES stock solution. The preparations were incubated at 40° C. for the indicated times, and then the samples were removed and frozen to −80° C. Samples were thawed for analysis of β-glucocerebrosidase activity. Table 6 shows enzyme activity over time. FIG. 7 shows activity at the time points as a percent of initial activity (T0; 0 hr).

TABLE 6

Effect of HES on Promoting GCR Activity

| GCR HES Study | Activity (U/mL) | | |
|---|---|---|---|
| Time (hour) | 0% HES | 10% HES | 40% HES |
| 0 | 120.83 ± 3.76 | 118.59 ± 7.12 | 70.23 ± 8.05 |
| 1 | 45.23 ± 0.62 | 62.37 ± 1.15 | 94.69 ± 2.36 |
| 2 | 17.00 ± 0.13 | 29.88 ± 1.34 | 82.27 ± 3.80 |
| 3 | 7.64 ± 0.55 | 13.76 ± 0.6 | 69.15 ± 7.96 |
| 4 | 1.73 ± 0.02 | 6.07 ± 0.15 | 59.32 ± 2.39 |
| 6 | 0.57 ± 0.03 | 2.16 ± 0.08 | 51.30 ± 3.45 |
| 22 | 0.14 ± 0.01 | 0.32 ± 0.02 | 23.07 ± 0.01 |
| 48 | 0.09 ± 0.00 | 0.18 ± 0.00 | 20.72 |

Means and standard deviations from activity assays performed on duplicate samples.

The data in Table 6 indicate that the Target Enzyme, GCR containing 0% and 10% HES lost >95% of its activity under stressed conditions by 6 hours at 40° C. In contrast, the sample containing 40% HES maintained >50% of the initial activity in the same time period under the same stressed conditions. This data shows that the Target Enzyme, GCR, is stabilized by the presence of the polysaccharide HES.

Example 2

Effect of HES on α-glucosidase Stability

Figure 8:
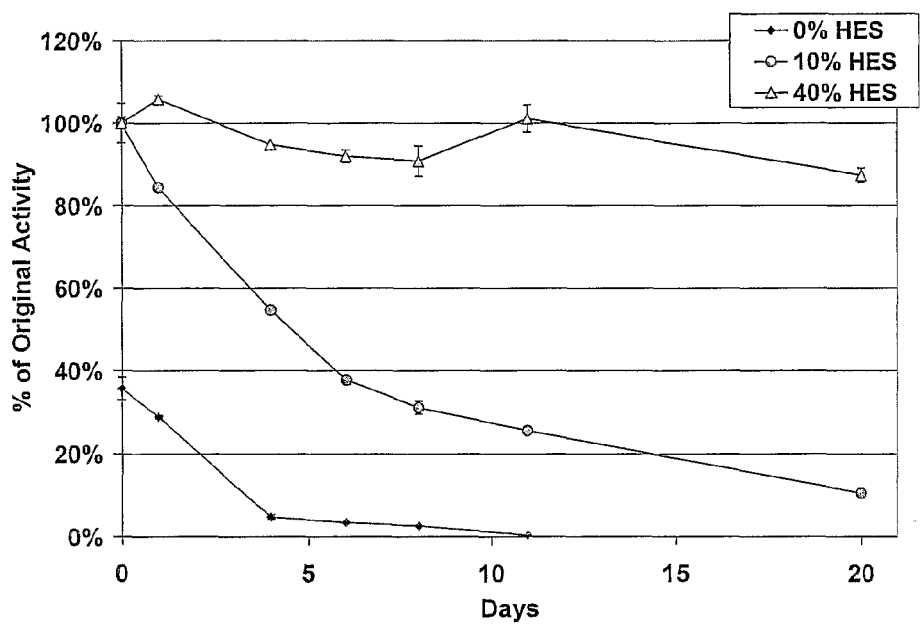
FIG. 8 is a graph of days versus % of original activity illustrating the effect of HES on promoting α-glucosidase stability.
Figure 9:
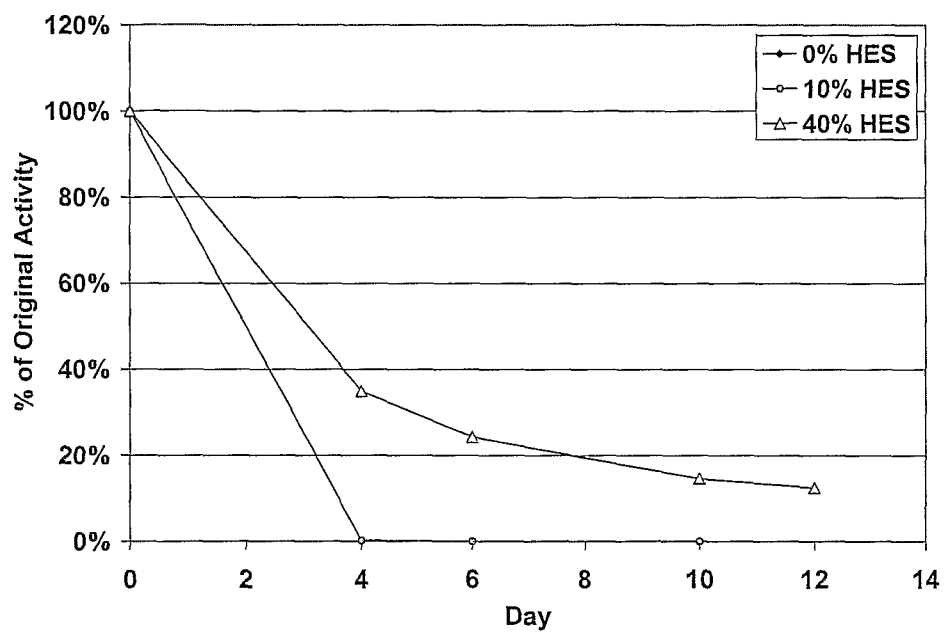
FIG. 9 is a graph of the effect of HES on promoting α-galactosidase stability.

A study was conducted to evaluate the effect of HES on the Target Enzyme α-glucosidase. Purified α-glucosidase was prepared in conditions intended to promote a loss of Target Enzyme enzymatic activity in the absence of a stabilizer such as HES. Specifically, the enzyme was prepared into 50 mM Sodium Acetate, pH 4.0 and then, solutions containing 0%, 10% and 40% HES and α-glucosidase were prepared by adding appropriate volumes of a 50% HES stock solution. The solutions were incubated at 40° C., and samples were removed at the indicated time points and then frozen to −80° C. Samples were thawed and analyzed for α-glucosidase activity Table 7 shows activity measured in the various samples over the time period of 0-20 days. FIG. 8 shows activity at the time points as a percent of initial activity (T0; Time zero).

TABLE 7

Effect of HES on Promoting α-glucosidase Activity

| αGlu HES Study | Activity (U/mL) | | |
|---|---|---|---|
| Time (Day) | 0% HES | 10% HES | 40% HES |
| 0 | 5.91 ± 0.46 | 18.36 ± 0.27 | 14.72 ± 0.71 |
| 1 | 4.78 ± 0.06 | 15.49 ± 0.18 | 15.58 ± 0.12 |
| 4 | 0.79 ± 0.01 | 10.0 ± 0.01 | 13.95 ± 0.01 |
| 6 | 0.57 ± 0.00 | 6.93 ± 0.17 | 13.54 ± 0.22 |
| 8 | 0.43 ± 0.01 | 5.71 ± 0.29 | 13.37 ± 0.54 |

TABLE 7-continued

Effect of HES on Promoting α-glucosidase Activity

| αGlu HES Study | Activity (U/mL) | | |
|---|---|---|---|
| Time (Day) | 0% HES | 10% HES | 40% HES |
| 11 | 0.06 ± 0.02 | 4.69 ± 0.12 | 14.89 ± 0.49 |
| 20 | nd | 1.92 ± 0.02 | 12.85 ± 0.26 | nd—no data
means and standard deviations from activity assays performed on duplicate samples.

A starting solution of Target Enzyme α-glucosidase, prior to buffer preparation into the pH 4.0 buffer, was expected to have about 16 U/ml. In the process of preparing the samples to pH 4.0 (~30 min to 1 h), the control sample, 0% HES, showed about a 63% decrease from its expected initial α-glucosidase activity The samples in 10% and 40% HES did not experience this activity loss. Only about 10% of the remaining activity in the 0% HES sample was demonstrated by day 4. The 10% HES sample maintained about 55% of its activity during the same time period and the 40% HES sample maintained essentially full activity through the entire study (20 days). This data shows that α-glucosidase is stabilized by the presence of HES.

Example 3

Effect of HES on Promoting α-galactosidase Stability

The Target Enzyme, α-galactosidase, was prepared at the same protein concentration in 50 mM sodium phosphate, pH 7.5 buffer containing 0%, 10% or 40% HES. The preparations were incubated at 40° C. for the indicated times, and then the samples were removed and frozen to −80° C. Samples were thawed and analyzed for α-galactosidase activity. Table 8 shows enzymatic activity over time. The control sample, 0% HES, showed essentially no activity at Day 3, whereas the 40% HES sample showed about 35% of its initial activity at Day 3 and about 13% at Day 12. This data shows that β-galactosidase is stabilized by the presence of HES.

TABLE 8

Effect of HES on Promoting α-galactosidase Stability

| αGal HES Study | Activity (U/mL) | | |
|---|---|---|---|
| Time (Day) | 0% HES | 10% HES | 40% HES |
| 0 | 307.2 | 310.7 | 374.2 |
| 4 | 0.3 | 0.7 | 130.6 |
| 6 | 0 | 0 | 90.9 |
| 10 | 0 | 0 | 54.7 |
| 12 | 0 | 0 | 46.9 |

Example 4

Compounds Tested for the Ability to Promote Enzymatic Activity

Five compounds were evaluated for their ability to promote the enzymatic activity of three Target Enzymes (sialidase, β-galactosidase, and β-hexosaminidase): (1) glycerol, (2) propylene glycol, (3) a soybean protein hydrolysate, HY-SOY™ (Quest International, Chicago, Ill.), (4) hydroxyethyl starch ("HES"), (B. Braun, Puerto Rico, unless otherwise indicated) and (5) Hmxl.

HES was prepared as a 20% (w/v) stock solution by dissolving solid HES into buffer of the appropriate pH. For this Example, 100 mM sodium citrate, 5 mM calcium chloride, pH 5.7 buffer was used. The 20% (w/w) stock solution was used to make a final concentration of 5% w/L sv HES in the Target Enzyme cocktails. Haemaccel (Hmxl) stock solutions (Aventis-Behring Gmdh, Marburg, GE) at a stock concentration of 3.5% were used in amounts as indicated in the Examples below. Glycerol and propylene glycol were added to 10% (w/v), and HY-SOY™, a dry powder, to 5% (w/v) to 100 mM codium citrate, 5 mM calcium chloride, pH 5.7 buffer.

Target Enzyme cocktails containing three Target Enzymes were made by combining sialidase (210 U/L sv), β-galactosidase (33 U/L sv), β-hexosaminidase (2500 U/L sv), and either Hmxl (14 mL/L sv) or HES (5% w/L sv). Each Target Enzyme cocktail was then separately processed as follows: The cocktail was loaded onto a Phenyl Sepharose™ column (at room temperature) previously equilibrated with 100 mM sodium citrate buffer containing 5 mM calcium chloride at pH 5.7, and then subsequently loaded with GCR substrate at 70 to 120 U GCR/mL of column resin. The enzymatic activity of GCR is measured using standard assays (see, e.g., U.S. Pat. No. 6,451,600). The substrate bound to the column. The Target Enzyme cocktail was then recirculated through the column at room temperature for approximately 24 hours. The Target Enzyme cocktail was then washed from the column, and the substrate was eluted with propylene glycol and collected. Results are shown in Table 9.

TABLE 9

Results of Tested Compounds

| Additive | % Modification (FACE Assay) |
| --- | --- |
| No additive | 53.1 |
| 0.05% Hmxl | 69.1 |
| 10% Glycerol | 34.2 |
| 10% Propylene glycol | 51.1 |
| 5% HES | 68.6 |
| 5% HY-SOY ™ | 57.2 |

The extent of oligosaccharide/polysaccharide modification was substantially increased in the presence of either Hmxl or hydroxyethyl starch (HES), as measured by fluorophore-assisted carbohydrate electrophoresis (FACE) (69.1 and 68.6, respectively; Table 9) as compared to the absence of the additives (53.1; Table 9). Thus, both Hmxl and HES were able to promote enzymatic activity of the Target Enzymes used in this reaction. The other three compounds tested either did not show Target Enzyme promotion (HY-SOY™ and propylene glycol) or showed a diminution of Target Enzyme promotion (glycerol).

Example 5

The Promotion of Target Enzyme Activity by Hmxl and HES

The same amount of the three Target Enzymes was used in each of the six experiments shown below in Table 10.

A mixture of sialidase (210 U/L sv), β-galactosidase (33 U/L sv), and β-hexosaminidase (2500 U/L sv) was examined with either no non-naturally occurring polysaccharide, or in the presence of Hmxl (14 ml/L sv) or HES (5% w/sv), at room temperature. The Target Enzyme cocktail was loaded onto a Phenyl Sepharose™ column previously equilibrated with 100 mM sodium citrate buffer containing 5 mM calcium chloride at pH 5.7, and then subsequently loaded with substrate at 70 to 120 U GCR/mL of column resin. The substrate bound to the column. The Target Enzyme cocktail was then recirculated through the column at room temperature for approximately 24 hours. After approximately 24 hours, the Target Enzyme cocktail was washed from the column, and the substrate was eluted and collected and assayed by FACE analysis. Results are shown in Table 10.

TABLE 10

The Promotion of Target Enzyme Activity in the Presence of Hmxl or HES

| Exp. # | Sialidase U/L sv | β-gal U/L sv | β-hex U/L sv | pH | HES % w/L sv | Hmxl mL/L sv | FACE |
| --- | --- | --- | --- | --- | --- | --- | --- |
| 1 | 210 | 33 | 2500 | 5.7 | 0 | 0 | 54.4 |
| 2 | 210 | 33 | 2500 | 5.7 | 0 | 14 | 70.4 |
| 3 | 210 | 33 | 2500 | 5.7 | 0 | 14 | 75.1 |
| 4 | 210 | 33 | 2500 | 5.7 | 5 | 0 | 84.5 |
| 5 | 210 | 33 | 2500 | 5.7 | 5 | 0 | 80.6 |

The Table 10 data demonstrate that both Hxml and HES can promote the enzymatic activity of the Target Enzyme, i.e., enhance the ability of the Target Enzymes to cause oligosaccharide/polysaccharide modification. The oligosaccharide/polysaccharide modification is substantially reduced in the absence of either Hxml or HES (see Table 10, Exp.# 1). Although both HES and Hxml are effective promoters of Target Enzyme activity, Hxml is an animal derived peptide, whereas HES is a polysaccharide derived from non-animal sources (e.g., plant). Therefore, the polysaccharides of this invention are particularly useful to promote the activity of a Target Enzyme in situations where animal components are not desirable, such as in the production or manufacture of human or veterinary therapeutics, foods or consumables.

Example 6

HES Promotion of Target Enzyme Activity Lowers the Amount of Target Enzymes Needed to Achieve Comparable Substrate Modification In this Example, the Target Enzyme cocktail used for oligosaccharide/polysaccharide modification contained 5% w/L sv HES, or did not contain HES.

For the HES-containing Target Enzyme cocktails, sialidase (105 U/L sv), β-galactosidase (β-gal, 16.5 U/L sv), and α-hexosaminidase (β-hex, 1250 U/L sv) in 100 mM sodium citrate, 5 mM calcium chloride, pH 5.5was added to HES (final HES amount of 5% w/L sv).

For the Target Enzyme cocktails, prepared in the absence of a non-naturally occurring polysaccharide, sialidase (168 U/L sv), β-galactosidase (52.8 U/L sv), and β-hexosaminidase (3000 U/L sv) were combined in 100 mM sodium citrate, 5 mM calcium chloride, pH 5.5.

All cocktails were held at 2-10° C. until use. Each Target Enzyme cocktail was then separately processed as follows:

The Target Enzyme cocktail was added to a Phenyl Sepharose™ column that had been equilibrated with 100 mM sodium citrate buffer containing 5 mM calcium chloride at pH 5.5 and then loaded with substrate (70 to 120 U GCR/mL resin), at room temperature. The Target Enzyme cocktail was recirculated through the column for approximately 24 hours. The column was then washed with one column volume of equilibration and then with five column volumes of buffer containing 20% propylene glycol, to remove the Target Enzymes cocktail. The substrate was eluted from the column with propylene glycol. The resulting oligosaccharide components of each of the seven test reactions was evaluated by FACE assay, and is shown in Table 11.

TABLE 11

Promotion of Target Enzyme Activity on a GCR Substrate in the Presence of HES at pH 5.5

| Exp. # | Sialidase U/sv | β-gal U/sv | β-hex U/sv | HES (%/sv) | FACE |
|---|---|---|---|---|---|
| 1 | 168 | 52.8 | 3000 | 0 | 69.4 |
| 2 | 168 | 52.8 | 3000 | 0 | 69.9 |
| 3 | 168 | 52.8 | 3000 | 0 | 70.0 |
| 4 | 168 | 52.8 | 3000 | 0 | 71.8 |
| 5 | 105 | 16.5 | 1250 | 5 | 72 |
| 6 | 105 | 16.5 | 1250 | 5 | 72.7 |
| 7 | 105 | 16.5 | 1250 | 5 | 72.7 |

The three experiments in the presence of 5% HES (Exp. #5-7), required substantially lower amounts of the three Target Enzymes to achieve oligosaccharide/polysaccharide modification, in comparison to the experiments performed in the absence of HESS (Exp. # 1-4). The mean FACE value for the four test reactions in the absence of HES was 70.3+/−1.1, whereas the mean FACE value for the experiments in the presence of HES was 72.5+/−0.4. Importantly, the Target Enzyme cocktails without additive contained 1.6× (where 'x' is the multiple of) the amount of sialidase, 3.2× the amount of β-galactosidase, and 2.4× the amount of β-hexosaminidase as compared to the HES Target Enzyme cocktails. Thus, in the absence of HES, the process requires considerably increased amounts of Target Enzymes.

In another study (see Table 12), the Target Enzyme cocktail was used with an oligosaccharide/polysaccharide modification reaction which contained 5% w/L sv HES, or did not contain HES.

A 20% (w/w) HES stock solution, produced by dissolving solid HES into 100 mM sodium citrate, 5 mM calcium chloride, pH 5.5, was used to make a final concentration of 5% w/L sv HES in a cocktail containing the units of enzyme shown in the Table 12, in 100 mM sodium citrate, 5 mM calcium chloride, pH 5.5.

For the Target Enzyme cocktails, prepared in the absence of a non-naturally occurring polysaccharide, the cocktails were prepared to contain the units of enzyme (U/L sv) shown in the Table 12.

The cocktails were held at 2-10° C. until use. Each Target Enzyme cocktails was then separately processed as follows:

The Target Enzyme cocktail was added to a Phenyl Sepharose™ column that had been equilibrated with 100 mM sodium citrate buffer containing 5 mM calcium chloride at pH 5.5 and then loaded with substrate (70 to 120 U GCR/mL resin), at room temperature. The Target Enzyme cocktail was recirculated through the column for approximately 24 hours. After the oligosaccharide modification, the column was washed to remove the Target Enzyme cocktail. The substrate was eluted from the column using propylene glycol. The resulting oligosaccharide component of each of the five test reactions was evaluated by FACE assay. Results are shown in Table 12.

TABLE 12

Lower Amounts Of Target Enzymes Required In Reactions Containing HES

| Exp. # | Sialidase U/sv | β-gal U/sv | β-hex U/sv | HES (%/sv) | FACE |
|---|---|---|---|---|---|
| 1 | 168 | 52.8 | 3000 | 0 | 69.4 |
| 2 | 105 | 16.5 | 1250 | 5 | 72.0 |
| 3 | 168 | 52.8 | 3750 | 0 | 77.1 |
| 4 | 84 | 19.8 | 1500 | 5 | 76.9 |
| 5 | 210 | 33 | 2500 | 5 | 85.0 |

The data in Table 12 demonstrate that comparable (or higher) FACE values were obtained with lesser amounts of Target Enzymes in reactions containing HES. e.g., compare: Exp.# 1 versus Exp.# 2; also compare e.g., Exp.# 3 versus Exp.# 4. Furthermore, to achieve a higher FACE of 85 in the presence of HES (Exp.# 5), which is a FACE value that is 7.9% higher than that for Exp.# 3 (performed in the absence of a Target Enzyme promoter), 38% less β-galactosidase, 33% less β-hexosaminidase, and only a modest increase in sialidase to 25% was needed in the HES-containing Exp.# 5.

Example 7

HES is Compatible with a Variety of Target Enzyme Concentrations

The conditions employed in this example were as described in Example 6, except that all experiments included HES 5% w/L sv.

TABLE 13

Increasing Target Enzyme Level Increases Oligosaccharide/Polysaccharide Substrate (GCR) Modification

| Exp. # | Sialidase U/sv | B-gal U/sv | β-hex U/sv | FACE |
|---|---|---|---|---|
| 1 | 84 | 13.2 | 1000 | 67.4 |
| 2 | 84 | 13.2 | 1500 | 72.8 |
| 3 | 105 | 16.5 | 1500 | 74.1 |
| 4 | 84 | 19.8 | 1500 | 76.9 |
| 5 | 210 | 33 | 2500 | 85.0 |

The data in Table 13 demonstrate that increasing the amount of Target Enzymes in HES, increases the oligosaccharide/polysaccharide modification. The FACE value increased by 17.6%, from 67.4 (Exp.# 1) to 85.0 (Exp.# 5) by a 2.5× increase of sialidase, β-galactosidase, and β-hexosaminidase. Thus, HES is compatible with a variety of enzyme concentrations.

Example 8

The Effect of pH on Target Enzyme Promotion

The conditions employed in this Example were as described in Example 7, except that the pH (of the Target Enzyme cocktail, equilibration buffer, and column washes) was at the pH designated in Table 14 and the presence of HES was as indicated in Table 14.

TABLE 14

Effect of pH on Target Enzyme Promotion

| Exp. # | Sialidase U/sv | β-gal U/sv | β-hex U/sv | pH | HES (%/sv) | FACE |
|---|---|---|---|---|---|---|
| 1 | 126 | 19.8 | 1500 | 5.5 | 5 | 75.3 |
| 2 | 210 | 39.6 | 1500 | 5.7 | 5 | 75.8 |
| 3 | 210 | 66 | 3750 | 5.7 | 0 | 76.0 |
| 4 | 252 | 79.2 | 4500 | 5.9 | 0 | 72.2 |

The pH of an enzymatic modification reaction can have an effect on the oligosaccharide profile of a substrate. In the absence of HES, even when increased amounts of Target Enzymes are used, a comparable FACE was not obtained when the pH was increased from 5.7 to 5.9 (see Exp. # 3 and Exp. # 4; Table 14). In the presence of HES, increasing the pH from 5.5 to 5.7 required only modest increases in Target Enzyme levels to achieve comparable FACE values at both pHs, (compare Exp.# 2 versus Exp. #1). Additionally, the inclusion of HES into the Target Enzyme cocktail, reduced the amount of Target Enzyme needed to achieve comparable FACE at a given pH (e.g., compare Exp. #2 and Exp. #3). This indicates that a non-naturally occurring polysaccharide such as HES allows a lower amount of Target Enzymes to be used across a pH range, and therefore, broadens the pH range at which a Target Enzyme may be used to obtain its desired activity.

Example 9

Increasing HES Concentration Improves Target Enzyme Promotion

The conditions employed in this Example were as described in Example 8, except that the pH of the Target Enzyme cocktail, equilibration buffer, and column washes were at pH 5.5, the Target Enzyme cocktail contained either 2% or 5% HES w/L sv, and the Target Enzyme amounts were identical to each other for both experiments.

TABLE 15

Effects of HES Concentrations

| Exp. # | Sialidase U/sv | β-gal U/sv | β-hex U/sv | HES (%/sv) | FACE |
|---|---|---|---|---|---|
| 1 | 210 | 33 | 2500 | 2 | 77.3 |
| 2 | 210 | 33 | 2500 | 5 | 85.0 |

The data in Table 15 indicate that increasing HES concentration from 2% to 5% improves Target Enzyme promotion. In this Example, FACE values increased 7.7%, when HES increased from 2% to 5%.

Further, the data indicate that HES promotes Target Enzyme activity at a 2% concentration. In the absence of HES, at pH 5.5, Target Enzyme amounts of 79.2 U/L sv of β-galactosidase (2.4× the amount in Exp. #1, of Table 15), and 3000 U/L sv of β-hexosaminidase (1.2× the amount in Exp. #1, of Table 15) were required for comparable FACE value (76.9, Exp.#1 77.3; using the same conditions employed as in Table 15, except as to Target Enzyme concentration).

Example 10

HES from Different Commercially Available Sources, and Different AMW and MS, Promotes Target Enzyme Activity HES from two additional commercially available sources, Ajinomoto (Raleigh, N.C., USA), and Fresenius Kabi (Linz, Austria), was compared to HES from B. Braun for the promotion of Target Enzyme activity in an oligosaccharide/polysaccharide modification reaction.

The conditions employed in this Example were as described in Example 10, except that the pH of the Target Enzyme cocktail, equilibration buffer, and column washes was at pH 5.7, and the Target Enzyme cocktail contained HES at 5% w/L sv from either B Braun, Ajinomoto, or Fresenius Kabi. The Target Enzyme amounts were identical for each experiment within Table 16 (210 U/L sv of sialidase, 39.6 U/L sv of β-galactosidase, and 1500 U/L sv of β-hexosaminidase).

Three different lots of Ajinomoto HES and three different lots of Fresenius Kabi HES were compared to HES from B Braun. The Ajinomoto HES is commercially available in an average molecular weight (AMW) in a range of 550-760 kDa, and a molar substitution (MS) of 0.70-0.80 molar. Fresenius Kabi HES is commercially available in a average molecular weight in the range of 400-500 kDa and a molar substitution of 0.65-0.75. The manufacturer's indicated AMW and MS for the lots of HES used in the study are shown in Table 16.

TABLE 16

Promotion of Target Enzyme Activity using HES from Three Different Vendors

| Manufacturer | Lot | Replicate (n) | Manufacturer's AMW (kd)/(MS) | FACE |
|---|---|---|---|---|
| B. Braun | 1 | 1 | 546/(0.76) | 73.7 |
| Ajinomoto | 1 | 3 | 654/(0.8) | 74.0 +/− 2.8 |
| Ajinomoto | 2 | 1 | 684/(0.76) | 70.1 |
| Ajinomoto | 3 | 1 | 701/(0.76) | 75.4 |
| Mean | | 5 | na | 73.5 +/− 2.8 |
| Fresenius Kabi | 1 | 2 | 448/(0.72) | 72.7 +/− 6.9 |
| Fresenius Kabi | 2 | 1 | 455/(0.71) | 77.3 |
| Fresenius Kabi | 3 | 1 | 424/(0.69) | 74.4 |
| Mean | | 4 | na | 74.3 +/− 4.5 | na = not applicable

The data in Table 16 indicate that comparable promotion of Target Enzyme activity was found using HES purchased from B. Braun, Ajinomoto, and Fresenius Kabi. Thus, slight variations in HES AMW, and MS, between lots of HES from the same vendor, and from different vendors, were found not to significantly affect HES promotion of the Target Enzymes activity toward its substrate.

Example 11

HES Promotion of Target Enzyme Activity is Independent of System Volume (sv)

The conditions employed in this Example were as described in Example 10, except that HES from only B. Braun was used for the experiments. The Target Enzyme amounts were identical for each experiment in Table 17, namely: 210 U/L sv of sialidase, 39.6 U/L sv of β-galactosidase, and 1500 U/L sv of β-hexosaminidase. The "Scale" indicated reflects a comparison between the volume of the systems used in each experiment shown in Table 17 (including volume occupied by the phenyl resin and piping). For example, a system volume of 1500× means that the system volume is 1500 times greater than a 1× system volume (sv).

TABLE 17

HES Promotion of Target Enzyme Activity In Different System Volumes

| Scale (sv) | Replicates (n) | FACE |
|---|---|---|
| 1x | 3 | 77.7 +/- 2.7 |
| 1500x | 3 | 76.7 +/- 1.9 |

The data in Table 17 indicate that HES promotion of Target Enzyme activity is independent of system volume scale. In this Example, HES promotion of Target Enzyme activity is effective and comparable within a wide range of system volume. Thus, the invention is applicable to a variety of industrial and commercial scale enzyme processes.

Example 12

Effect of HES on α-galactosidase Stability in Buffer

A prophetic study is conducted to evaluate the effect of HES on α-galactosidase stability. α-galactosidase at about 5.0 mg/ml in 50 mM Sodium Phosphate, pH 7.0 containing either 0%, 10% or 40% hydroxylethyl starch is aseptically filtered into an appropriate container and held at 25° C. for up to 12 months. Sterile samples are removed at 0, 3, 6, 9, and 12 months and frozen to −80° C. Samples are thawed for analysis and assayed by an α-galactosidase activity assay. Table 18 shows activity at the time points as a percent of initial activity (T0).

TABLE 18

Effect of HES on Promoting α-galactosidase Stability in Buffer

| α-galactosidase HES Study | | Activity (% T0) | | | |
|---|---|---|---|---|---|
| HES Concentration | T0 | 3 months | 6 months | 8 months | 12 months |
| 0% (control) | 100 | less than 50% of T0 activity | less than 50% of T0 activity | less than 50% of T0 activity | less than 50% of T0 activity |
| 10% | 100 | 50% or greater increase over control | 50% or greater increase over control | 50% or greater increase over control | 50% or greater increase over control |
| 40% | 100 | 50% or greater increase over control | 50% or greater increase over control | 50% or greater increase over control | 50% or greater increase over control |

α-galactosidase samples containing 10% and 40% HES retain minimally 50% or greater activity than α-galactosidase samples that do not contain HES. Accordingly, α-galactosidase is stabilized by the presence of HES.

Example 13

Effect of HES on α-galactosidase Stability in Buffer and Mannitol

A prophetic study is conducted to evaluate the effect of HES on α-galactosidase stability. α-galactosidase at 5.0 mg/ml in 50 mM Sodium Phosphate, 3% mannitol (w/w), pH 7.0, containing either 0%, 10% or 40% HES is aseptically filtered into an appropriate container and held at 25° C. for up to 12 months. Sterile samples are removed at 0, 3, 6, 9, and 12 months and frozen to −80° C. Samples are thawed for analysis and assayed by an α-galactosidase activity assay. Table 19 shows activity at the time points as a percent of initial activity (T0).

TABLE 19

α-galactosidase HES, Study Activity Data

| α-galactosidase HES Study | | Activity (% T0) | | | |
|---|---|---|---|---|---|
| HES Concentration | T0 | 3 months | 6 months | 8 months | 12 months |
| 0% (control) | 100 | less than 50% of T0 activity | less than 50% of T0 activity | less than 50% of T0 activity | less than 50% of T0 activity |
| 10% | 100 | 50% or greater increase over control | 50% or greater increase over control | 50% or greater increase over control | 50% or greater increase over control |
| 40% | 100 | 50% or greater increase over control | 50% or greater increase over control | 50% or greater increase over control | 50% or greater increase over control |

α-galactosidase samples containing 10% and 40% hydroxy ethyl starch retain minimally 50% or greater activity than α-galactosidase samples that do not contain HES. Accordingly, α-galactosidase is stabilized by the presence of HES.

Example 14

Effect of HES on α-galactosidase Stability After Reconstitution of Freeze Dried Product with Water Containing HES A prophetic study is conducted to evaluate the stability of freeze dried α-galactosidase after reconstitution in water containing either 0%, 10% or 40% HES and the presence, or absence of a suitable preservative such as benzyl alcohol or phenol. α-galactosidase at 5.0 mg/ml in 50 mM Sodium Phosphate, 3% mannitol, pH 7.0 is freeze dried into appropriate containers (vials). The reconstituted vials are held at 25° C. and a, sample is removed at 0, 5, 10, 20, and 30 days and assayed by a pNP assay. Table 20 shows activity at the time points as a percent of initial activity (T0).

TABLE 20

Effect of HES on α-galactosidase Stability after Reconstitution of Freeze Dried Product with Water Containing HES

| α-galactosidase HES Study HES Concentration | T0 | Activity (% T0) | | | |
|---|---|---|---|---|---|
| | | 5 days | 10 days | 20 days | 30 days |
| 0% (control) | 100 | less than 50% of T0 activity | less than 50% of T0 activity | less than 50% of T0 activity | less than 50% of T0 activity |
| 10% | 100 | 50% or | 50% or | 50% or | 50% or |

TABLE 20-continued

Effect of HES on α-galactosidase Stability after Reconstitution of Freeze Dried Product with Water Containing HES

| α-galactosidase HES Study HES Concentration | T0 | Activity (% T0) | | | |
|---|---|---|---|---|---|
| | | 5 days | 10 days | 20 days | 30 days |
| 40% | 100 | greater increase over control 50% or greater increase over control | greater increase over control 50% or greater increase over control | greater increase over control 50% or greater increase over control | greater increase over control 50% or greater increase over control |

α-galactosidase samples containing 10% and 40% HES retain minimally 50% or greater activity than α-galactosidase samples that do not contain HES. Accordingly, α-galactosidase is stabilized by the presence of HES.

Accordingly, the Examples herein demonstrate a wide range of utility for the compositions and methods of the invention.

Other embodiments of the invention will be apparent to those skilled in the art from consideration of the specification and practice of the invention disclosed herein. It is intended that the specification and Examples be considered as exemplary only, with the true scope and spirit of the invention being indicated by the following claims.

All publications and patent documents cited in this disclosure are incorporated by reference in their entirety. The citation of any references herein is not an admission that such references are prior art to the present invention. All concentrations of polysaccharides are expressed as volume per weight, unless otherwise indicated.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of promoting enzymatic activity of a target enzyme comprising:
   (a) combining a target enzyme wherein the target enzyme is one or more oligosaccharide/polysaccharide enzymes, lysosomal hydrolases or a combination thereof with a hydroxyalkyl starch and a substrate of the target enzyme, thereby producing a composition, wherein the composition comprises about 0.01% to about 55% w/v of the hydroxyalkyl starch wherein the hydroxyalkyl starch is not conjugated to the target enzyme or the substrate; and
   (b) maintaining the composition under conditions in which enzymatic alteration of the substrate by the target enzyme occurs, thereby promoting the enzymatic activity of the target enzyme.

2. The method of claim 1 wherein the target enzyme is in a liquid milieu.

3. The method of claim 1 wherein the composition is maintained without freezing for a period of time.

4. The method of claim 1 wherein the target enzyme is an enzyme that acts on oligosaccharide(s)/polysaccharide(s).

5. The method of claim 1, wherein the hydroxyalkyl starch is hydroxyethyl starch (HES).

6. The method of claim 1, wherein the composition is maintained at a temperature between about 1° C. and about 40° C.

7. The method of claim 1, wherein the substrate is an enzyme.

8. The method of claim 7, wherein the enzyme that is the substrate is a lysosomal hydrolase.

9. The method of claim 8, wherein the lysosomal hydrolase is β-glucocerebrosidase.

10. The method of claim 1, wherein the target enzyme is selected from the group consisting of: sialidase, β-galactosidase, β-N-acetylhexosaminidase and a combination thereof; the hydroxyalkyl starch is hydroxyethyl starch (HES); and the substrate is β-glucocerebrosidase.

11. The method of claim 10, wherein a modified substrate is produced and the modified substrate is recovered.

12. A method of promoting the enzymatic activity of sialidase, β-galactosidase, and β-hexosaminidase comprising:
   (a) combining the sialidase, β-galactosidase, and β-hexosaminidase with a substrate of the sialidase, β-galactosidase and β-hexosaminidase and hydroxyethyl starch (HES), thereby producing a composition, wherein the composition comprises between about 1% and about 12% w/v of the HES wherein the HES is not conjugated to the sialidase, β-galactosidase, and β-hexosaminidase or the substrate; and
   (b) maintaining the composition under conditions in which the sialidase, β-galactosidase, and β-hexosaminidase modify the substrate, thereby promoting the enzymatic activity of sialidase, β-galactosidase and β-hexosaminidase.

13. A method of promoting enzymatic activity of a target enzyme comprising:
   (a) combining a target enzyme wherein the target enzyme is one or more oligosaccharide/polysaccharide enzymes, lysosomal hydrolases or a combination thereof with a hydroxyalkyl starch and a substrate of the target enzyme, thereby producing a composition, wherein the composition comprises about 0.01% to about 55% w/L sv of the hydroxyalkyl starch wherein the hydroxyalkyl starch is not conjugated to the target enzyme or the substrate; and
   (b) maintaining the composition under conditions in which enzymatic alteration of the substrate by the target enzyme occurs, thereby promoting the enzymatic activity of the target enzyme.

14. The method of claim 13 wherein the target enzyme is in a liquid milieu.

15. The method of claim 13 wherein the composition is maintained without freezing for a period of time.

16. The method of claim 13 wherein the target enzyme is an enzyme that acts on oligosaccharide(s)/polysaccharide(s).

17. The method of claim 13, wherein the hydroxyalkyl starch is hydroxyethyl starch (HES).

18. The method of claim 13, wherein the composition is maintained at a temperature between about 1° C. and about 40° C.

19. The method of claim 13, wherein the substrate is an enzyme.

20. The method of claim 19, wherein the enzyme that is the substrate is a lysosomal hydrolase.

21. The method of claim 20, wherein the lysosomal hydrolase is β-glucocerebrosidase.

22. The method of claim 13, wherein the target enzyme is selected from the group consisting of: sialidase, β-galactosidase, β-N-acetylhexosaminidase and a combination thereof; the hydroxyalkyl starch is hydroxyethyl starch (HES); and the substrate is β-glucocerebrosidase.

23. The method of claim 22, wherein a modified substrate is produced and the modified substrate is recovered.

* * * * *